United States Patent
Dockrill et al.

(10) Patent No.: US 10,549,271 B2
(45) Date of Patent: Feb. 4, 2020

(54) COVER MEMBER, METHOD AND TREATMENT MODULE FOR TREATING A BIOLOGICAL SAMPLE ON A SUBSTRATE

(71) Applicant: LEICA BIOSYSTEMS MELBOURNE PTY LTD, Mt. Waverley, Victoria (AU)

(72) Inventors: Mark Brian Dockrill, Chadstone (AU); Anthony Favaloro, Richmond (AU); Kenneth Heng-Chong Ng, Donvale (AU); Martin Limon, Richmond (AU); Peter Toogood, Vermont (AU); Stephen John Bagnato, Mt. Waverley (AU)

(73) Assignee: LEICA BIOSYSTEMS MELBOURNE PTY LIMITED, Mount Waverly, Victoria (AU)

( * ) Notice: Subject to any disclaimer, the term of this patent is extended or adjusted under 35 U.S.C. 154(b) by 230 days.

(21) Appl. No.: 14/357,888

(22) PCT Filed: Nov. 15, 2012

(86) PCT No.: PCT/AU2012/001407
§ 371 (c)(1),
(2) Date: May 13, 2014

(87) PCT Pub. No.: WO2013/071352
PCT Pub. Date: May 23, 2013

(65) Prior Publication Data
US 2014/0315256 A1    Oct. 23, 2014

Related U.S. Application Data

(60) Provisional application No. 61/560,543, filed on Nov. 16, 2011.

(51) Int. Cl.
*B01L 3/00* (2006.01)

(52) U.S. Cl.
CPC .............. *B01L 3/502* (2013.01); *Y10T 436/25* (2015.01)

(58) Field of Classification Search
CPC ........ B01L 3/502; B01L 3/5027; G01N 1/312
(Continued)

(56) References Cited

U.S. PATENT DOCUMENTS 5,346,672 A * 9/1994 Stapleton .............. B01L 3/5027
                                                                422/559
5,681,741 A * 10/1997 Atwood ............... B01J 19/0046
                                                                422/566
(Continued)

FOREIGN PATENT DOCUMENTS

CN    1672030 A    9/2005
JP    4507295 A    12/1992
(Continued)

OTHER PUBLICATIONS

Translation of Communication dated Mar. 19, 2015, issued by the State Intellectual Property Office of the People's Republic of China in corresponding Chinese Application No. 201280067038X.
(Continued)

*Primary Examiner* — Jill A Warden
*Assistant Examiner* — Jacqueline Brazin
(74) *Attorney, Agent, or Firm* — Sughrue Mion, PLLC

(57) ABSTRACT

A cover member for a substrate supporting a biological sample comprises first and second opposing ends, first and second opposing surfaces, a void in the second surface which, when juxtaposed with a substrate, forms a chamber, and a fluid inlet toward the first end and in fluid communication with the void. The void is bounded by void walls having one or more contoured regions for enhancing fluid
(Continued)

movement within the chamber. A treatment module for a biological sample comprises the cover member, a support surface for a substrate bearing the biological sample and clamp means operable to releasably retain the cover member in juxtaposition with the substrate for an incubation period. A method for incubating the biological sample with one or more reagents uses the cover member.

35 Claims, 16 Drawing Sheets

(58) Field of Classification Search
    USPC .......................................................... 422/560
    See application file for complete search history.

(56) References Cited

U.S. PATENT DOCUMENTS

| | | | | |
|---|---|---|---|---|
| 5,989,386 | A | * | 11/1999 | Elliott ................. B65H 3/0816 |
| | | | | 156/285 |
| 6,474,386 | B2 | * | 11/2002 | Takahashi ............ C04B 35/536 |
| | | | | 156/362 |
| 6,673,620 | B1 | * | 1/2004 | Loeffler ................. B01L 3/502 |
| | | | | 359/398 |
| 2004/0235148 | A1 | * | 11/2004 | Shibazaki .......... B01L 3/50255 |
| | | | | 435/287.2 |
| 2007/0243603 | A1 | | 10/2007 | Einsle et al. |
| 2008/0229812 | A1 | * | 9/2008 | Hund .................... G01Q 30/20 |
| | | | | 73/105 |

FOREIGN PATENT DOCUMENTS

| | | | |
|---|---|---|---|
| JP | 11502926 | A | 3/1999 |
| JP | 2005530165 | A | 10/2005 |
| JP | 2005530208 | A | 10/2005 |
| JP | 200778490 | A | 3/2007 |
| WO | 9102962 | A1 | 3/1991 |
| WO | 9107486 | A1 | 5/1991 |
| WO | 9319207 | A1 | 9/1993 |
| WO | 2004/001389 | A1 | 12/2003 |
| WO | 2004001390 | A1 | 12/2003 |
| WO | WO 2004001389 | * | 12/2003 |
| WO | 2011008415 | A2 | 1/2011 |
| WO | WO 2011008415 | * | 4/2011 |
| WO | 2011060387 | A1 | 5/2011 |
| WO | 2011069507 | A1 | 6/2011 |

OTHER PUBLICATIONS

Communication dated Apr. 14, 2015, issued by the Australian Intellectual Property Office in corresponding Australian Application No. 2012339616.
Communication dated Jun. 3, 2015, issued by the European Patent Office in corresponding European Application No. 12849833.4.
Communication dated Oct. 4, 2016, issued by the Japan Patent Office in corresponding Japanese Application No. 2014-541480.
European Examination Report; EP Appln. No. 12849833.4-1371; dated May 12, 2016.
Chinese Office Action; Third Office Action; CN Application No. 201280067038X; dated Jul. 29, 2016.
Chinese Office Action; Second Office Action; CN Application No. 201280067038X; dated Jan. 14, 2016.
Japanese Office Action; JP Appln No. 2014-541480; dated Oct. 4, 2016.
Japanese Decision of Refusal; JP Appln. No. 2014-541480; dated Jun. 6, 2017.
Canadian Office Action; Application Serial No. 2,855,511; dated Jul. 3, 2018.

* cited by examiner

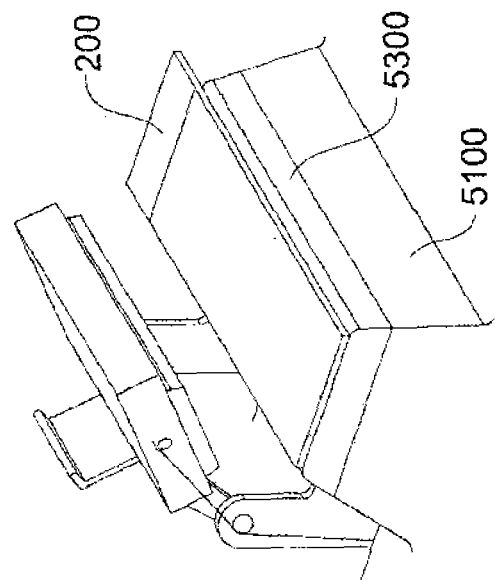
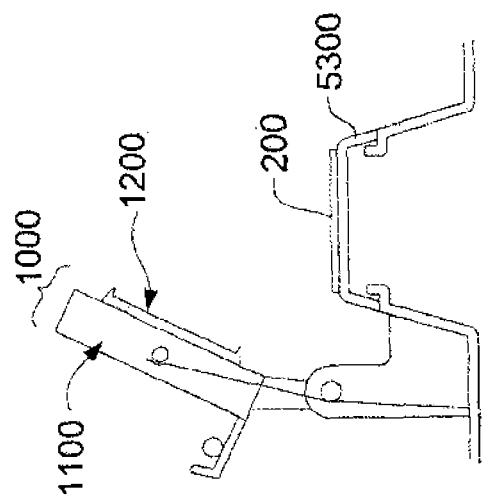
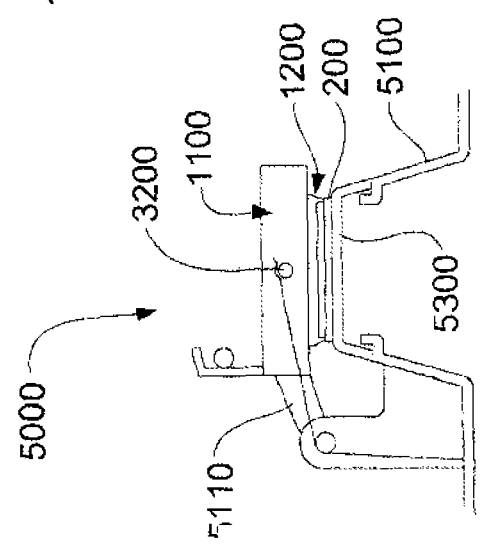

COVER MEMBER, METHOD AND TREATMENT MODULE FOR TREATING A BIOLOGICAL SAMPLE ON A SUBSTRATE

CROSS REFERENCE TO RELATED APPLICATIONS

This application is a National Stage of International Application No. PCT/AU2012/001407 filed Nov. 15, 2012, claiming benefit of U.S. Patent Application No. 61/560,543 filed Nov. 16, 2011, the contents of all of which are incorporated herein by reference in their entirety.

FIELD OF THE INVENTION

This invention relates to instrumentation and methods for automated staining of anatomical pathology samples. It relates particularly, but not exclusively to, a cover member which forms a reagent chamber over a substrate, such as a slide on which a pathology sample has been placed.

BACKGROUND TO THE INVENTION

Instrumentation for automated treatment of biological samples, such as anatomical pathology samples, is well known. Treatment may include staining procedures of the kinds that are typical in immunochemistry, in-situ hybridisation, special staining and cytology. Automation of some staining procedures has increased the speed with which pathology testing can be completed leading to earlier diagnosis and in some cases, intervention. Staining is typically performed on samples placed on microscopy slides to highlight certain histological features in a biological sample and incubation of the sample with small volumes of reagent is often performed. In many cases, automated staining of samples involves manipulation of robotic arms to deliver an aliquot of reagent to achieve staining. While automation has many advantages, there are also limitations associated with automating these procedures.

In some cases staining achieved by automated instrumentation is patchy or unreliable leading to rejection or "failure" of some slides by the pathologist. Failure can be attributable to bubbles forming in the reagent which leads to uneven stains, and/or debris from reagents producing lower quality stains. In other cases the cost to run each test is prohibitively high typically because of the high cost of purchasing and maintaining the instrumentation and/or the reagents used. In other cases still, stained areas are too small relative to the sample size and are not useful for diagnostic analysis.

Complexity of the automated instrumentation can also be problematic with myriad moving parts requiring calibration, maintenance and cleaning. In many cases processed sample throughput is limited by batch processing regimes where sample processing times are limited by the slowest staining protocol being administered in the batch.

It would be desirable to improve upon the available approaches to automated treatment of biological samples or at least provide a viable alternative to methods and devices used.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge in the patent area as at the priority date of any of the claims.

SUMMARY OF THE INVENTION

Viewed from one aspect, the present invention provides a cover member for a substrate supporting a biological sample, the cover member comprising:
 a) first and second opposing ends;
 b) first and second opposing surfaces;
 c) a void in the second surface which, when juxtaposed with a substrate, forms a chamber; and
 d) a fluid inlet toward the first end and in fluid communication with the void;
wherein the void is bounded by void walls having one or more contoured regions for enhancing fluid movement within the chamber.

Preferably, the cover member includes a fluid outlet toward the second end and in fluid communication with the void and through which fluid may be withdrawn.

In one or more embodiments, the one or more contoured regions comprise rounded corners that connect side walls of the void with an end wall. In one embodiment, the contoured regions may comprise rounded corners toward the second end of the cover member to encourage fluid removal from the chamber. In another embodiment, the contoured regions may comprise rounded corners connecting side walls of the void with an end wall toward the first end of the cover member to encourage fluid flow within the chamber. In yet another embodiment, the one or more contoured regions may comprise rounded cornices connecting the walls of the void with a void ceiling in the second surface of the cover member. In another embodiment still, the one or more contoured regions may comprise a taper or obround-like end region which joins opposing side walls of the void.

The cover member may provide a volume, when the chamber is closed of e.g. 30 to 200 μl, preferably 50 to 150 μl and more preferably about 100 μl to about 125 μl. In one or more embodiments, the chamber has a height of 50 to 200 μm. In some embodiments, the height is preferably 100 to 150 μm. In certain embodiments, the cover member includes a reservoir at the inlet which has a volume sufficient to receive one or more aliquots of a fluid to be dispensed into the chamber for a step in a treatment protocol.

The second surface has a void ceiling which, in various embodiments, has a finish that enhances reagent propagation from the inlet to the outlet. The finish may be e.g. a texture selected from a group including: etched, corrugated, dimpled, sloped, bowed and rippled. Alternatively the finish may be a material finish or coating on at least the part of the void ceiling and/or walls.

Preferably, the cover member is adapted to be retained in juxtaposition with the substrate during a treatment protocol. In some embodiments, the cover member is disposable or semi-disposable (e.g. used for 5, 10, 15 or 20 protocols before being replaced). In other embodiments, the cover member is formed from at least two parts including a cover member body and a cover member insert, where the cover member insert is configured to form the chamber with the substrate. In this arrangement, the cover member insert may be disposable.

In some embodiments, the cover member includes a moisture barrier configured to reduce drying out of a sample on a substrate with which the cover member is used. The moisture barrier may take any suitable form which does not interfere with the sample on the substrate. For example, the moisture barrier may be a material shroud adapted to cover but not contact the sample on the slide. Alternatively, the moisture barrier may be a vapour barrier which prevents the sample on the substrate from dehydrating.

In one embodiment, the cover member includes guide means at the inlet, configured to direct fluid into the inlet. Preferably the guide means comprises a neck shaped to receive a correspondingly shaped dispensing probe tip so that they form mating contact for forced dispensing of a fluid from the probe into the inlet. Thus, the neck may have a decreasing taper towards the second surface which accommodates the probe tip. Ideally, the guide means is configured to form a snug fit with a dispensing probe tip. This may be achieved by providing the guide means with compliance sufficient to receive and form a seal with a dispensing probe tip although in another arrangement the probe tip is compliant.

In another embodiment, the cover member has a dispersing edge disposed in fluid communication with the inlet. In use the cover member is adapted to pivot about the dispersing edge and the pivoting motion causes movement of fluid in the inlet from the dispersing edge toward the outlet. The cover member may be further adapted to pivot about an axis extending therethrough and perpendicular to a plane extending orthogonally between the first and second ends, wherein pivoting about said axis tilts the cover member. It may be desirable to tilt the cover member to prevent premature release of fluid in the inlet, or to gain access to a slide beneath the cover member, when in an open condition In another embodiment still, the cover member includes a fluid dispersing feature configured to disperse fluid from the inlet onto at least a width of the chamber formed in the cover member. Preferably, the fluid dispersing feature comprises a channel spanning a width of the chamber. In one embodiment the channel has a stepped profile with increasing height toward the first end of the cover member. Ideally, the channel is configured to store a volume of fluid from the inlet. The stored fluid feeds a fluid front which is gradually spread onto the substrate.

The fluid dispersing feature may be configured to disperse fluid in a closed condition or in an open condition. For open dispensing, the fluid dispersing feature is configured to disperse fluid during relative sliding movement of the cover member and the substrate from an open condition in which the sample is outside the chamber, to a closed condition in which the cover member covers at least a portion of the sample on the substrate, thereby drawing fluid from the dispersing feature along the substrate surface. In a closed condition, the cover member overlaps at least a portion of the sample on the substrate and capillary action draws fluid from the dispersing feature along the substrate surface.

The cover member may further comprise sliding guide means configured to guide the substrate during relative sliding movement of the cover member and substrate between the open and closed conditions. Ideally, the sliding cover member also includes a moisture barrier configured to reduce drying out of a sample on a substrate with which the cover member is used. The moisture barrier may be a physical material barrier or a vapour or other barrier adapted to minimise sample drying.

Viewed from another aspect, the present invention provides a treatment module for a biological sample, the module comprising:
  a. a cover member according to any one of the preceding claims;
  b. a support surface for a substrate having a biological sample thereon; and
  c. clamp means operable to releasably retain the cover member in juxtaposition with the substrate for an incubation period.

The clamp means applies a clamping force sufficient to prevent leakage of reagent from the space between the substrate and the cover member during a protocol, whilst not damaging or breaking the substrate. Clamping forces may be in the range of e.g. approximately 3 N to 300 N. In some instances higher clamping forces may be difficult to achieve, e.g. when a plurality of treatment modules are incorporated into an automated instrument. Thus it may be desirable to use a lower clamping force e.g. 250 N or 100 N. Clamping forces as low as 10 N may also be used. In one form, the clamp means comprises a resilient member biased to retain the cover member in juxtaposition with the substrate. In various embodiments, the treatment module also provides substrate retention means configured to retain the substrate on the supporting surface during opening of the chamber e.g. to overcome the forces of "sticktion".

In one or more embodiments the support surface comprises a thermal exchanger configured to control the temperature of a biological sample on the substrate during a treatment protocol. It is to be understood, however, that the thermal exchanger may form part of a cover member described above, or may be coupled with a cover member.

Typically, the treatment module includes a robot configured to position one or both of the substrate and the cover member in the treatment module, and may also be configured to dispense reagent into an inlet of the cover member during a treatment protocol. In various embodiments the treatment module includes a coupling operable to interchangeably connect one or more outlets of the cover member with a vent to atmosphere and a respective one or more negative pressure sources. Typically, the one or more negative pressure sources generate a controlled vacuum of between −2 kPa and −15 kPa. The one or more negative pressure sources may be controlled by a controller device programmed to apply a negative pressure for a duration of e.g. 1000 ms to 5000 ms, and preferably for about 2000 ms to 3000 ms.

The treatment module may be configured for use with an automated sample processing instrument comprising a plurality of treatment modules operable independently under control of a controller of the instrument. Ideally, the clamp means, thermal exchanger, robot, negative pressure sources and fluid dispensers and other components with which the treatment module are used are also under the control of the instrument controller.

In one embodiment, the treatment module includes pivot means configured to pivot the cover member about a dispersing edge on the cover member causing fluid in the inlet to move from the dispersing edge toward the outlet, and wherein the pivot means is operable to pivot the cover member to an open condition and to a closed condition in which the cover member and substrate are juxtaposed to form a chamber.

Preferably the pivot means is a pivot arm operable to position the cover member in the open condition wherein a dispersing edge of the first end of the cover member is in contact with the substrate and the second surface is disposed at an angle of 1 to 20 degrees to the substrate. The pivot means may also be operable to agitate reagent within the chamber. In an embodiment, the pivot arm is operable to position the cover member in the open condition such that the substrate and the second surface are disposed at an angle to receive an aliquot of fluid in the cover member inlet. In an embodiment, the substrate and second surface are disposed at an angle of approximately 5 to 60 degrees. In an embodiment, the substrate and second surface are disposed at an angle of approximately 8 to 25 degrees. In an embodiment, the substrate and second surface are disposed at an angle of approximately 10 degrees. The pivot arm may also be operable to dispose the module in a release condition in which the cover member and the substrate are disassociated, and/or to cause the cover member to tilt about a tilt axis extending through the cover member and perpendicular to a plane extending orthogonally between the first and second ends. Tilting may provide access to the substrate within the treatment module, and/or may preclude premature release of fluid from the inlet into the chamber. In one form, tilt bias means are provided for biasing the tilt direction of the cover member about the tilt access.

The treatment module may further include a wash bay for exposing the cover member second surface to a wash reagent. Thus, the support surface may be shaped to receive a substrate having a sample thereon and, in the absence of a substrate, to form the wash bay.

In one embodiment, the treatment module includes an actuator for slidingly moving the cover member and the substrate between an open condition in which the sample is not covered by the cover member, and a closed condition in which at least part of the sample is covered in a chamber formed by the cover member and the substrate. The treatment module may also include a moisture barrier as described above.

Viewed from another aspect, the present invention provides a cover member for a substrate supporting a biological sample, the cover member comprising:
  a. first and second opposing ends;
  b. first and second opposing surfaces;
  c. a void in the second surface which, when juxtaposed with a substrate, forms a chamber;
  d. a fluid inlet toward the first end and in fluid communication with the void;
  e. a fluid outlet toward the second end and in fluid communication with the void; and
  f. guide means at the inlet, configured to direct fluid into the inlet.

The guide means may comprise a neck shaped to receive a correspondingly shaped dispensing probe tip. The neck may have a decreasing taper towards the second surface and/or compliance. In any event, it is desirable that the guide means is configured to form a snug fit with the dispensing probe tip.

Viewed from yet another aspect, the present invention provides a method for incubating a biological sample with one or more reagents using a cover member with a guide means, including the steps of:
  a. providing the sample on a substrate;
  b. positioning the substrate and the cover member to form the chamber;
  c. positioning a dispensing probe tip in mating contact with the fluid inlet; and
  d. driving a first volume of a first reagent into the inlet with force sufficient for the first reagent to substantially cover the sample on the substrate.

The first reagent may be forced into the inlet by a positive pressure pump, such as a syringe pump or a gear pump, coupled to the dispensing probe tip.

The method may alternatively/additionally include the steps of:
  a. providing the sample on a substrate;
  b. positioning the substrate and the cover member to form the chamber;
  c. positioning a dispensing probe tip to dispense reagent into the fluid inlet; and
  d. dispensing at least second volume of a second reagent into the inlet.

The method may further include application of a negative pressure at the outlet to draw reagent within the chamber toward the outlet. Typically, the first reagent (being a reagent that is delivered into the inlet with a driving force), is a high value reagent while the second reagent (being a reagent is that is dispensed into the inlet without a driving force) is a low value reagent. The method may further include the step of tilting the cover member to elevate the outlet thereby limiting or precluding premature release of reagent from the inlet into the chamber.

Viewed from yet another aspect, the present invention provides a cover member for a substrate supporting a biological sample, the cover member comprising:
  a. first and second opposing ends;
  b. first and second opposing surfaces;
  c. a void in the second surface which, when juxtaposed with a substrate, forms a chamber;
  d. a fluid inlet toward the first end and in fluid communication with the void and; and
  e. a fluid outlet toward the second end and in fluid communication with the void;
  f. a dispersing edge disposed in fluid communication with the inlet;
wherein the cover member is adapted to pivot about the dispersing edge, and wherein in use said pivoting motion causes movement of fluid in the inlet from the dispersing edge toward the outlet.

The cover member may further provide a moisture barrier configured to reduce drying out of a sample on a substrate with which the cover member is used, as described above. Similarly, the cover member may provide a reservoir at the inlet having a volume sufficient to receive one or more aliquots of a reagent.

Viewed from another of its aspects, the present invention provides a treatment module for a biological sample, the module comprising:
  a. a cover member having a dispersing edge;
  b. a support surface for a substrate having a biological sample thereon; and
  c. pivot means configured to pivot the cover member about the dispersing edge causing fluid to move from the inlet along the substrate from the dispersing edge toward the outlet;
wherein the pivot means is operable to pivot the cover member to an open condition and to a closed condition in which the cover member and substrate are juxtaposed to form a chamber.

The pivot means may take any suitable form. In a preferred embodiment the pivot means comprises a pivot arm operable to position the cover member in the open condition wherein a dispersing edge of the first end of the cover member is in contact with the substrate and the second surface is disposed at an angle of 1 to 20 degrees to the substrate. Preferably the pivot arm is operable to position the cover member in the open condition such that the substrate and the second surface are disposed at an angle of approximately 10 degrees to receive an aliquot of reagent in the cover member inlet. The pivot arm may also be operable to cause the cover member to tilt about a tilt axis extending through the cover member and perpendicular to a plane extending orthogonally between the first and second ends. The pivot means may also be operable to dispose the module in a release condition in which the cover member and the substrate are disassociated and/or to agitate reagent within the chamber.

The treatment module may also include tilt bias means for biasing the tilt direction of the cover member about the tilt access and/or substrate retention means configured to releasably retain the substrate on the supporting surface during separation of the cover member and the substrate. The substrate retention means may comprise a resilient member configured to releasably retain the substrate on the supporting surface with a force sufficient to overcome a sticktion force between the cover member and the substrate during separation.

Ideally, the treatment module further comprises clamp means for releasably retaining the cover member in the closed condition. A wash bay, for exposing the cover member second surface to a wash reagent, may also be provided. In an embodiment, the support surface is shaped to receive a substrate having a sample thereon and, in the absence of a substrate, forms the wash bay. The treatment module may also provide a moisture barrier. In one or more embodiments the treatment module has a coupling operable to interchangeably couple one or more outlets of the cover member with one or more respective negative pressure sources.

Viewed from another aspect still, the present invention provides a method for incubating a biological sample with one or more reagents using a treatment module as just described, including the steps of:
 a. providing the sample on a substrate;
 b. positioning the substrate and the cover member in an open condition in which the cover member is angled such that the dispersing edge contacts the substrate;
 c. dispensing a first reagent into the inlet; and
 d. pivoting the cover member toward the closed condition, the pivoting action causing the dispensed reagent to substantially cover the sample on the substrate.

Ideally, the pivoting action is controlled at a rate which enhances capillary flow of the reagent to substantially cover the sample on the substrate. A negative pressure applied at the outlet may assist in drawing reagent within the chamber toward the outlet. A negative pressure may be used to evacuate and/or agitate fluid in the chamber. Various steps may be achieved using a controller according to a pre-programmed pivoting action that enhances reagent flow over the substrate for a plurality of reagents and/or for a plurality of protocols for treating a sample.

The method may further include the step of removing the slide from the support surface and immersing the second surface of the cover member in a wash reagent.

Viewed from another of its aspects, the present invention provides a cover member for a substrate supporting a biological sample, the cover member comprising:
 a. first and second opposing ends;
 b. first and second opposing surfaces;
 c. a void in the second surface for forming a chamber with the substrate;
 d. a fluid inlet toward the first end and in fluid communication with the void; and
 e. a fluid dispersing feature from which fluid is dispensed;
wherein the fluid dispersing feature is configured to dispense fluid from the inlet onto at least a width of the substrate.

In one embodiment the fluid dispersing feature comprises a channel spanning a width of the chamber. The channel may have a stepped profile with increasing height toward the first end of the cover member and may be configured to store a volume of fluid from the inlet where the stored volume of fluid feeds a fluid front which is gradually spread onto the substrate. The cover member may also provide an outlet toward the cover member second end, through which fluid may be withdrawn.

Preferably, the fluid dispersing feature is configured to dispense fluid during relative sliding movement of the cover member and the substrate from an open condition in which the sample is outside the chamber, to a closed condition in which the cover member covers at least a portion of the sample on the substrate, thereby drawing fluid from the fluid dispersing feature along the substrate. This may be referred to as "open dispensing".

Alternatively/additionally the fluid dispersing feature is configured to dispense fluid in a closed condition in which the cover member overlaps at least a portion of the sample on the substrate, wherein said dispersing utilises capillary action to draw fluid from the fluid dispersing feature along the substrate surface. This may be referred to as "closed dispensing".

The cover member may further comprise sliding guide means configured to guide the substrate during relative sliding movement of the cover member and substrate between open and closed conditions. A moisture barrier configured to reduce drying out of a sample on a substrate with which the cover member is used may also be provided.

Viewed from another aspect, the present invention provides a method for incubating a biological sample with one or more reagents using a cover member having a fluid dispersing feature, comprising the steps of:
 a. providing the sample on a substrate;
 b. positioning the substrate and the cover member in an open configuration in which at least an end portion of the substrate is disposed in juxtaposition with the second surface of the cover member in the region of the fluid dispersing feature;
 c. dispensing a reagent into the inlet and utilising capillary action to draw the reagent across the substrate.

Preferably the method including sliding one of the substrate and the cover member with respect to the other of the substrate and the cover member from an open condition in which the sample is outside the chamber, to a closed condition in which the cover member covers at least a portion of the sample within the chamber, wherein said sliding action draws the reagent from the dispersing feature along the substrate. Ideally, the sliding action is controlled at a rate which enhances flow of the reagent to substantially cover the sample on the substrate. The fluid may be dispensed into the inlet while the substrate and cover member are in the open condition ("open dispensing") or after they are in a respectively closed condition ("closed dispensing").

A vacuum may be applied to draw reagent through the chamber from the inlet to the outlet to assist with fluid dispersing, or to evacuate or agitate fluid in the chamber. In one embodiment, the method includes shrouding the substrate to limit drying of the sample when the cover member and substrate are re-opened.

Viewed from another aspect still, the present invention provides a treatment module for a biological sample, the module comprising:
 a. a cover member having a fluid dispersing feature;
 b. a support surface for a substrate having a biological sample thereon;
 c. a linear motion device for slidingly moving the cover member and the substrate between an open condition in which the sample is not covered by the cover member, and a closed condition in which at least part of the sample is covered in a chamber formed by the cover member and the substrate.

In one or more embodiments, the treatment module includes a wash bay for exposing the cover member second surface to a wash reagent during a wash step of a treatment protocol using the treatment module. A moisture barrier for protecting the sample may also be provided. The treatment module may also provide a coupling operable to interchangeably couple one or more outlets of the cover member with one or more respective negative pressure sources generating a vacuum.

BRIEF DESCRIPTION OF THE DRAWINGS

Embodiments of the invention will now be described in greater detail, by way of example only, with reference to the accompanying drawings. It is to be understood that the embodiments shown are examples only and may not be to scale in all instances. The examples discussed are not to be taken as limiting the scope of the invention as defined in the claims appended hereto. It is to be understood that the parts described are numbered in series (e.g. 1000, 2000, 3000), where like numerals generally designate like parts.

FIGS. 4a, c and d represent an end view taken in section through the inlet. FIG. 4b represents a top view of the cover member of FIG. 4a and FIG. 4e represents a top view of the cover member of FIGS. 4c and d.

FIGS. 6a to 6c are schematic illustrations of a treatment module according to an embodiment of the invention, with the cover member in a closed condition (FIG. 6a) and an open condition (FIGS. 6b and 6c).

DETAILED DESCRIPTION

It is desirable to perform incubation of small volumes of reagents on a substrate such as a microscope slide. Samples may be treated while slides are retained in a slide tray or individually at sample treatment modules.

Figure 1:
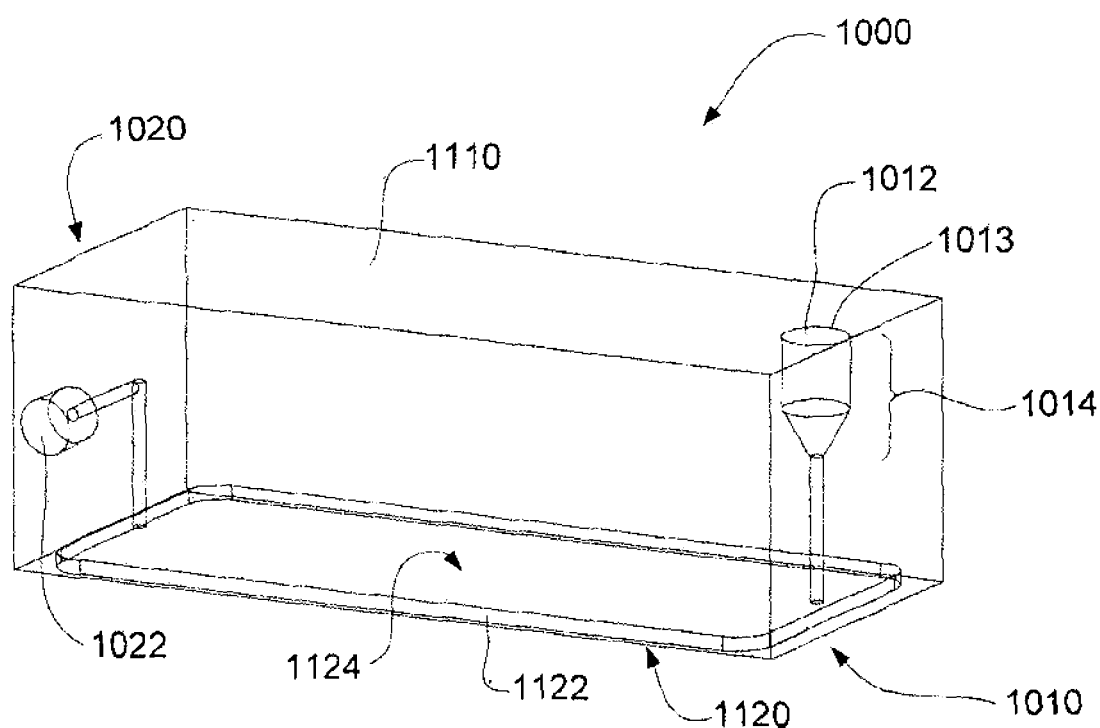
FIG. 1 is a schematic isometric view of a cover member according to an embodiment of the invention.

Referring firstly to FIG. 1, there is shown a cover member 1000 according to an embodiment of the invention, for use with a substrate 200 (shown in FIG. 2) for supporting a biological sample. For ease of reference, substrate 200 is hereinafter referred to as "slide" 200. The cover member has a first end 1010 and a second end 1020 and a first surface 1110 and a second surface 1120. A void 1124 is formed in the second surface, defined by a void boundary in the form of walls 1122 and a void ceiling 1140.

Figure 2:
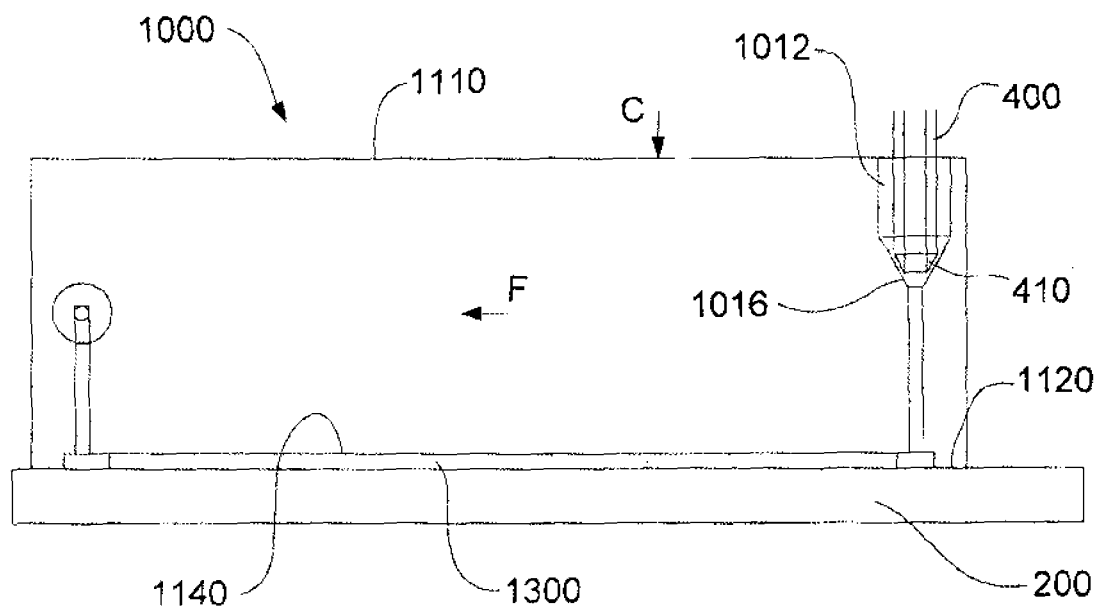
FIG. 2 is a side view of the cover member of FIG. 1 also showing a substrate in the form of a slide.

FIG. 2 is a side sectional view of the cover member 1000 and slide 200 disposed in juxtaposition to form a chamber 1300. A fluid inlet 1012 is provided toward the first end of the cover member and a fluid outlet 1022 is provided toward the second end of the cover member. The inlet and outlet are in fluid communication with the void 1124 so as to permit a reagent to enter the chamber through the inlet and exit via outlet 1022. A guide means 1014 is also provided at the inlet.

Figure 25:
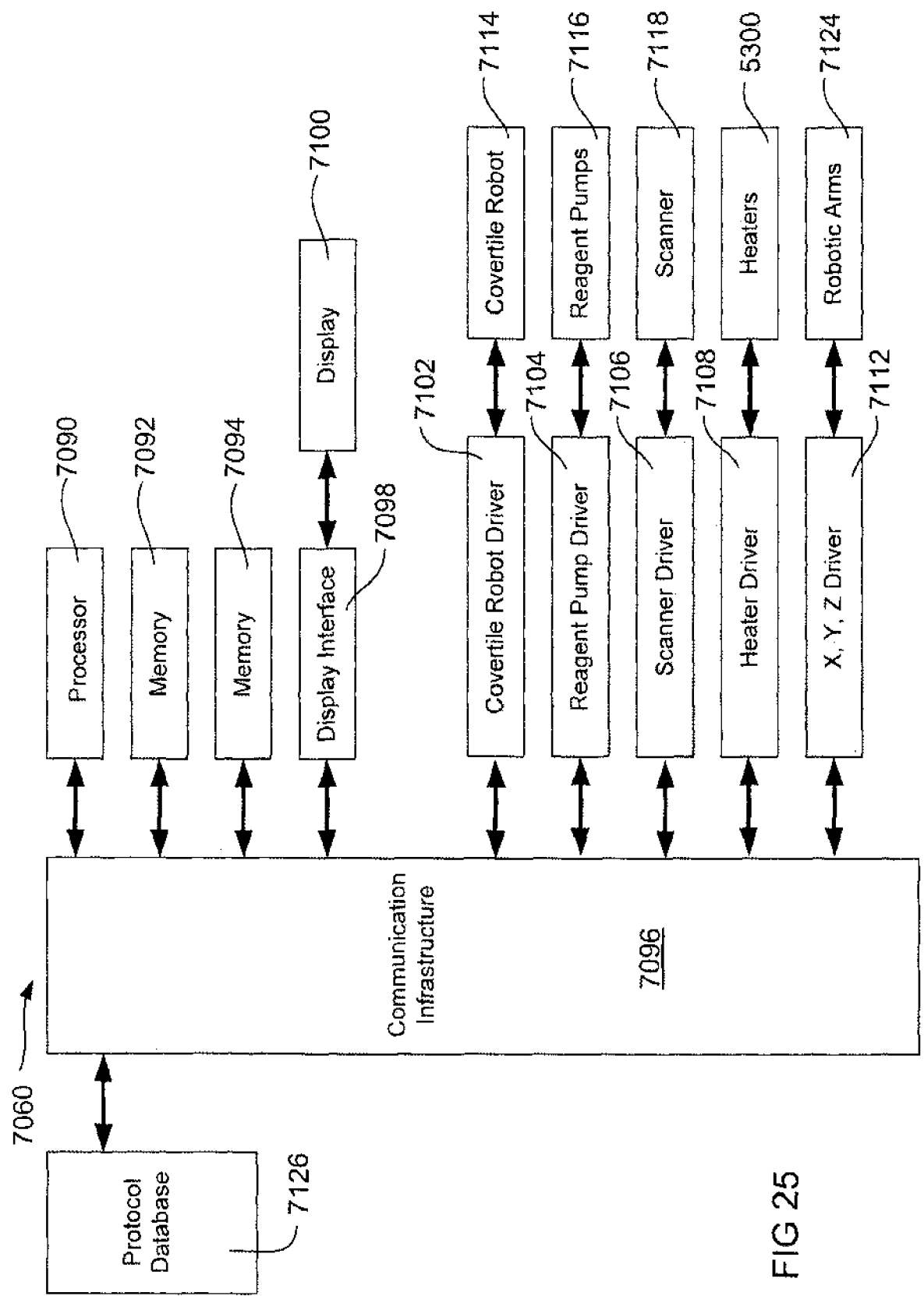
FIG. 25 is a schematic illustration of a controller for the instrument of FIG. 24.

In a preferred embodiment, the cover member 1000 is configured for use in an automated sample processing instrument 7000 such as the kind illustrated in FIG. 25. U.S. provisional patent applications 61/560,569 entitled "Biological Sample Treatment Apparatus" and 61/560,559 entitled "An Automated System and Method of Treating Tissue Samples on Slides" both filed concurrently with this application on 16 Nov. 2011 by the same applicant describe such instruments and the contents of those applications are hereby incorporated herein by reference.

The instrument uses a robotic arm to dispense a reagent into the cover member inlet. The guide means 1014 guides a dispensing probe 400 of the instrument into the inlet in such a way that the robotic controller need not precisely locate the probe tip 410 inside the inlet well. Rather, the controller need only position the probe tip 410 within the inlet opening 1013 and the guide means 1014 guides reagent dispensed from the probe tip through inlet 1012 and into the chamber 1300.

In a preferred embodiment, the guide means is configured for contact dispensing of reagent into the inlet. Thus, guide means 1014 comprises a neck 1016 which is shaped to receive a correspondingly shaped dispensing probe tip 410 (FIG. 2). The neck may be tapered to form e.g. a 45° angle to an axis running through the inlet and receives a correspondingly shaped dispensing probe tip 410 having a 45° angle between an axis extending through the probe 400 and the external probe tip walls. The correspondingly shaped probe tip 410 and neck 1016 cooperate to form a mating interface between the probe tip and the neck for dispensing of a reagent.

In one or more embodiments, the neck has compliance so that the mating interface provides a snug fit between the probe tip and the inlet neck to substantially preclude leakage of reagent forced into the inlet using positive pressure. However, use of a gasket or sealing ring at the mating interface is also contemplated. Compliance may be provided by a material property of the cover member including the neck, e.g. when the cover member is manufactured from a compliant material. Alternatively, there may be a compliant material coating in the neck area of the cover member or on the probe tip.

During dispensing of high value reagent, it is desirable that the dispensing probe tip 410 is brought into mating contact with the neck 1016 as described above. However, such contact may not be necessary for delivery of less expensive bulk fluid reagents such as DI water, alcohol, de-wax solution and the like. This is particularly the case when overdispensing (i.e. dispensing more than one aliquot of reagent) or cleaning. In an embodiment, cleaning involves non-contact dispensing of a cleaning reagent into the inlet and then withdrawing the reagent e.g. using a vacuum, back through the inlet or through the outlet when one is provided.

Figure 24:
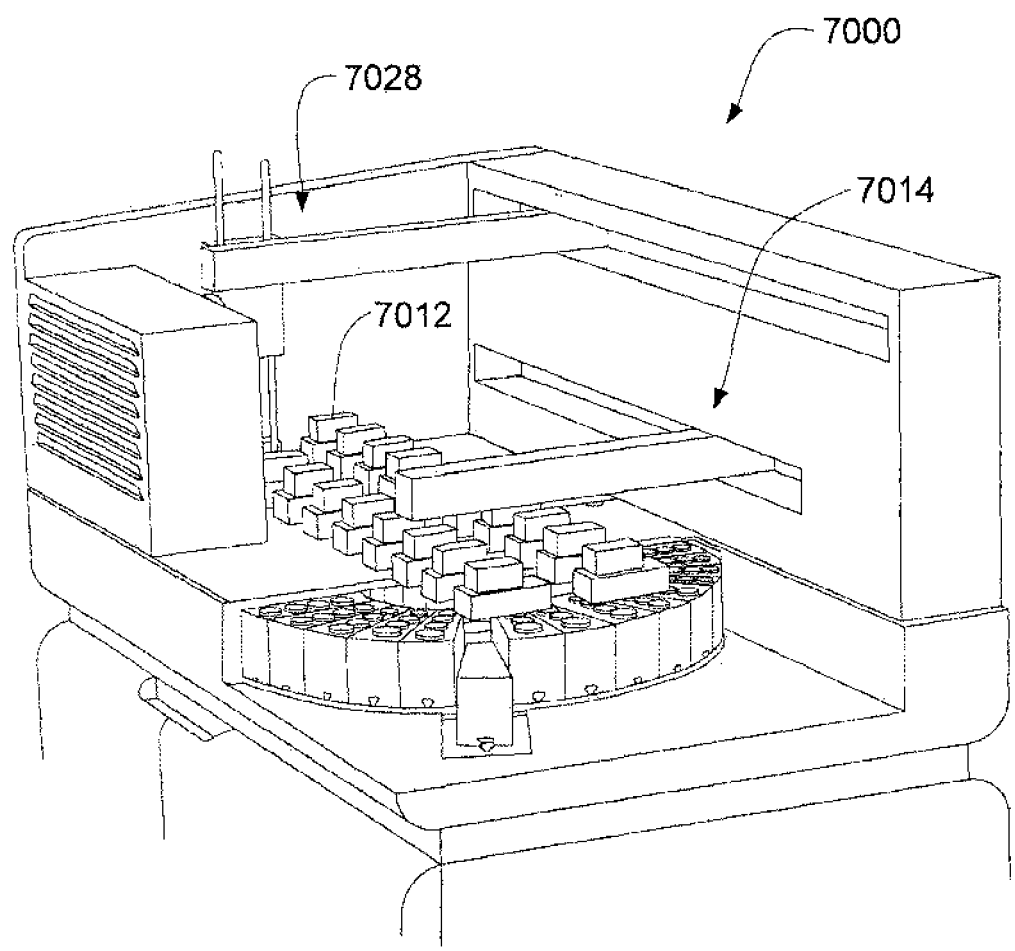
FIG. 24 is an example of an automated sample processing instrument with which embodiments of the invention may be used.

The dispensing probe may be e.g. a Fluid Transfer Probe (FTP) robot 7028 (using either a permanent or temporary pipette tip) or Bulk Fluid Robot (BFR) 7014 of an automated instrument 7000 such as the type illustrated in FIG. 24. In one embodiment, the FTP or BFR may also be used to position a cover member 1000 over a slide 200 so that they form chamber 1300 therebetween. In FIG. 24, a plurality of cover members are shown at individual sample treatment modules 7012 within the instrument 7000. Each of these may be controlled independently so that instrument throughput for individual treatment modules 7012 is not limited by incubation times required for protocols being performed on other modules in the instrument.

In this arrangement, the instrument may have reduced complexity since a dedicated robot for placement of the cover member is not necessary. Once the cover member is disposed in juxtaposition with a slide having a biological sample placed thereon, it is clamped into position using any suitable means and does not move for the duration of the treatment protocol. In FIG. 2, the arrow C designates the direction of a clamping force applied to the cover member to maintain its position during the protocol.

Advantageously, once the cover member 1000 is positioned and clamped in place, the cover member need not move relative to the slide 200 for the duration of the protocol. Use of a positive pressure to force reagent into the chamber and/or a vacuum to draw reagent through the chamber is sufficient for completing most protocols. Because the treatment protocol can be completed without moving the relative position of the cover member 1000 and the slide 200, there is minimal exposure of the sample to atmospheric air. Accordingly, the risk of sample dehydration is low and at the conclusion of a given protocol the sample may be coverslipped for transport and/or further processing.

Reagents may remain within the chamber for a period of incubation, before being withdrawn through outlet 1022. During incubation the temperature of the sample (and the reagent) may be modified e.g. by heating or cooling a thermal exchanger associated with the treatment module. Typically, the thermal exchanger is provided in the form of a heating/cooling pad 5300 (FIGS. 6a to 6c). Ideally, the thermal exchanger has the capacity to vary the temperature of the sample (and reagent in the chamber) within a range of 20 to 95 degrees Celsius, although higher temperatures (up to e.g. 120 degrees Celsius) may be required for some protocols. Some reagents may lead to bubble formation during heating steps. Typically, the bubbles migrate towards the inlet port 1012 and/or outlet port 1022 when vented to atmosphere. The rate of temperature change may be critical to the effectiveness of the protocol, e.g. in PCR where quick transitions are required. Ideally, the thermal exchanger accommodates those changes and also has the ability, in one or more embodiments, to cool. In various aspects of the invention the thermal exchanger is illustrated as a heating/cooling pad positioned below the slide. It is to be understood however that the thermal exchanger may be coupled with or incorporated into the cover member in various embodiments. For instance, the cover member may comprise a metal block with high thermal mass such that it may warm and actively cool samples (e.g. by refrigeration). Alternatively, the heating means may comprise heater pads, RF, microwave, and/or convection means and the cooling means may comprise chilling means, fins and/or a Peltier effect cooler. In further embodiments the cover member may heat and/or cool and the substrate support heat and/or cool in combination.

Typically, high value reagent is forced into the inlet in "contact mode" (i.e. with the probe tip in mating contact with the inlet) using a positive pressure pump such as a syringe pump. Preferably, operation of the syringe pump is under the control of a controller 7060 associated with the automated instrument 7000. Thus, once the probe tip 410 is matingly received within the neck 1014, the syringe pump is activated to deliver an aliquot of reagent into the chamber. With this approach, actively displacing reagent into the chamber using positive pressure minimises the amount of reagent required, and the time for reagent to enter the chamber and cover the sample on the slide.

During forced delivery of reagent into the chamber 1300, outlet 1022 is vented to atmospheric pressure. Controlling the rate of forced delivery provides control over the fluid front as it moves over the slide, thereby minimising the risk of bubble formation within the chamber. In some protocols, the reagent may be particularly viscous and propagation of the reagent across the slide surface within the chamber may be assisted by application of a vacuum at the outlet 1022. After the required incubation period, the reagent may be evacuated from the chamber by application of a vacuum at the outlet or by flushing with injection of a further reagent. Arrow F (FIG. 2) designates the direction of flow of reagents dispensed into the chamber. In order to provide the necessary pressure gradient across the chamber, a valve (not shown) may be provided and is operable to switchingly connect the outlet to atmospheric air or to a negative pressure source.

A typical treatment protocol involves dispensing bulk fluid reagents into the chamber to wash or otherwise treat the sample. During a wash step, it is desirable to flush the inlet 1012 to remove any residual high value reagent that may have adhered to the inlet walls e.g. during forced delivery of a high value reagent in contact mode. Accordingly, a probe dispensing bulk fluid reagents into the inlet 1012 need not make mating contact with the guide means/neck 1014. In various steps of a protocol it may be desirable for certain reagents to be dispensed in "non-contact mode" such that the mating surface is flushed.

Figure 3:
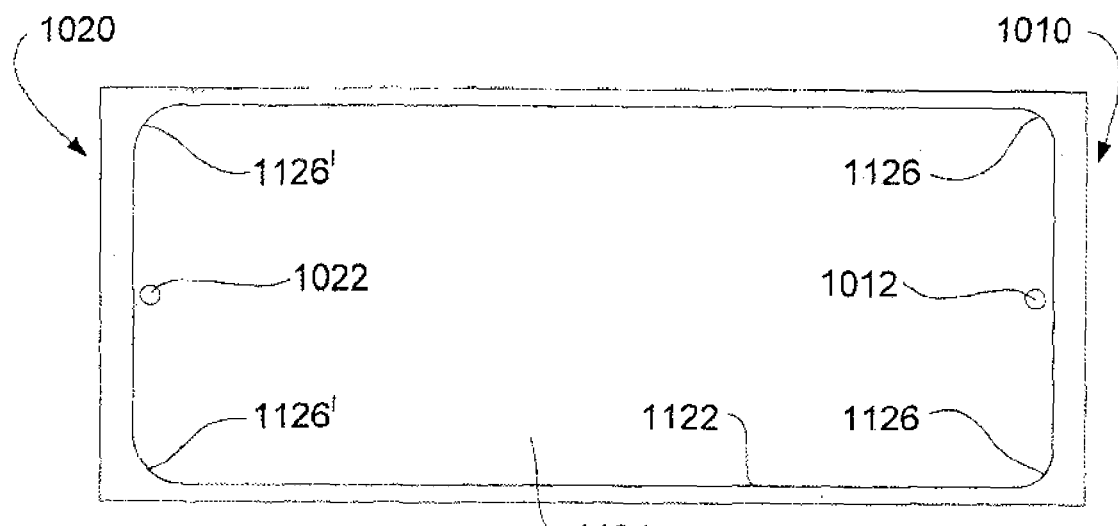
FIG. 3 is a schematic illustration of the second surface (underside) of the cover member of FIGS. 1 and 2.
Figure 4A:
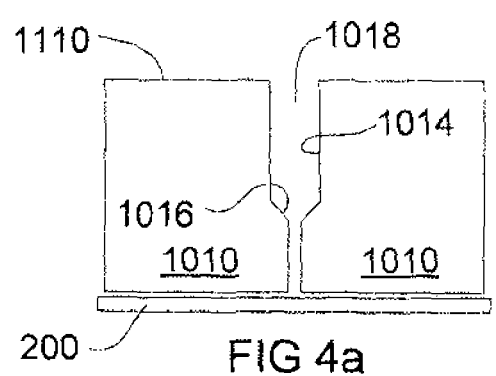
FIGS. 4a to 4e are schematic illustrations representing variations in the inlet shape of a cover member according to an embodiment of the invention.
Figure 4B:
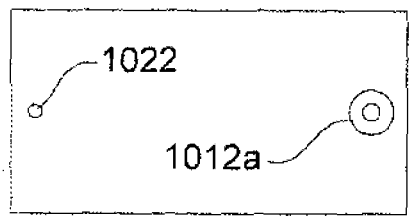
Figure 4C:
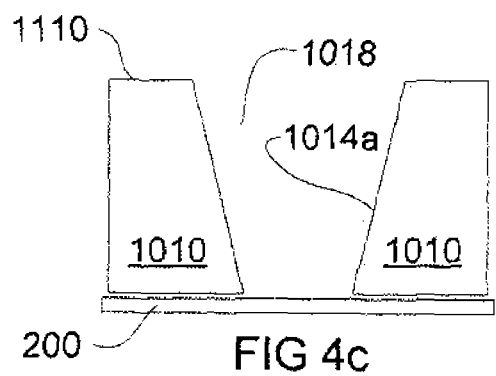
Figure 4E:
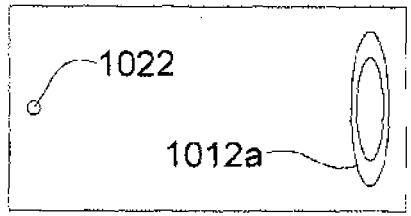
Figure 4D:
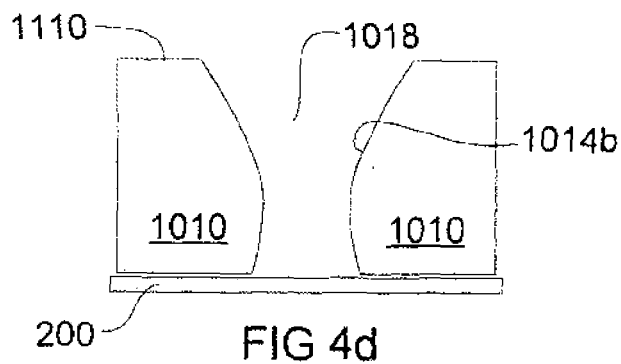

FIGS. 4a to 4e illustrate examples of different inlet profiles for the cover member 1000. FIGS. 4a, 4c and 4d represent end sectional views through the inlet 1012. FIG. 4b represents a top view of the cover member of FIG. 4a, and FIG. 4e represents a top view of the cover members of FIGS. 4b and 4c. As illustrated in FIGS. 4b and 4e, the outlet 1022 the outlet may exit the top of the cover member (i.e., through the first surface) or through the second end of the cover member as in FIGS. 1 to 3, or e.g. through a front or rear surface of the cover member.

FIG. 4a shows a variation of the inlet profile of the cover member of FIGS. 1-3, where guide means 1014 is extended to accommodate a larger volume of reagent thereby forming a reservoir 1018. Similar reservoirs 1018 are shown in the inlet profiles of FIGS. 4c and 4d. The reservoir 1018 has a volume sufficient to store more than one aliquot of reagent. An advantage of providing reservoir 1018 at inlet 1012 is to permit mixing of multiple reagents prior to entering the chamber 1300. Another advantage is that storing several dispenses of reagent may reduce the load on dispensing robots used in an automated instrument thereby reducing waiting time between steps in a protocol. Additionally, the larger, elliptical openings in FIGS. 4c and 4d reduce the complexity of movements performed by automated instrumentation robots to position reagent dispense nozzles since the dispensing target area is larger. To mitigate premature release of reagent from the reservoir 1018 into the chamber, a treatment module with which the cover member is used may be adapted to tilt the cover member to elevate the outlet thereby preventing release of the reagent into the chamber.

FIG. 3 is a schematic illustration of the second surface (underside) of the cover member of FIGS. 1 and 2. FIG. 3 shows contoured boundary walls at 1126. Contoured boundaries 1126 toward the first end assist with fluid flow within the chamber 1300. Contoured boundaries 1126' toward the second end 1020 militate against reagent and/or reagent debris remaining inside the chamber after washing or evacuation. Evacuation may be achieved by e.g., activation of a negative pressure source (i.e., vacuum) coupled to the outlet 1022 to withdraw or scavenge reagent from the chamber. Although in some embodiments the contoured boundaries may have the same geometric form, it is to be noted that this need not be the case. For instance, in FIG. 3 the contoured boundaries 1126 have a smaller radius than contoured boundaries 1126'. In another embodiment (not shown) the contoured boundaries may be merged to form a taper at one end (or both ends) of the void so that the void includes at one (or both) ends an obround-like or smooth arrowhead shape. However, inclusion of such a taper may reduce the area of the slide covered by the chamber and so limit the effectiveness of reagents dispensed into the chamber in slide staining.

In FIG. 3, inlet 1012 has similar diameter to outlet 1022 although this need not be the case. As can be seen in FIG. 4b, the diameter of the inlet opening into the void may be larger than the diameter of the outlet exiting the void.

Figure 5A:
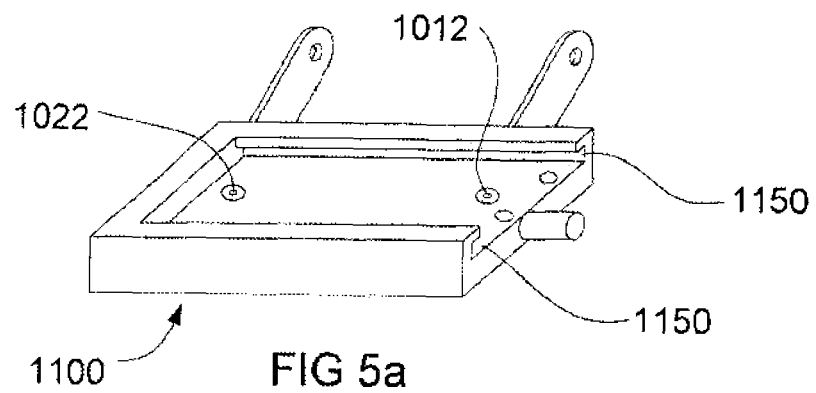
FIGS. 5a to 5c are schematic illustrations of cover member body, a cover member insert, and a cover member (comprised of a cover member body in combination with a cover member insert) respectively.
Figure 5B:
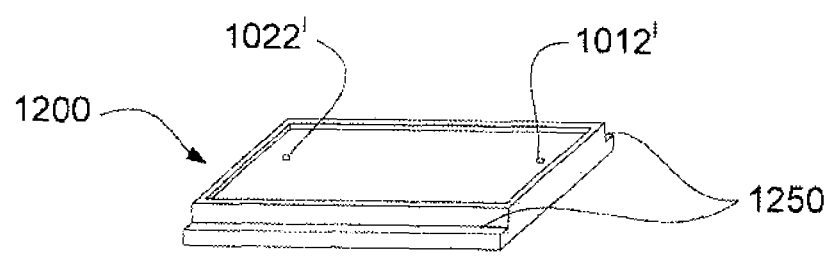

FIGS. 5a to 7b show an alternative embodiment of a cover member 1000 which is comprised of two parts: cover member body 1100 (FIG. 5a) and cover member insert 1200 (FIG. 5b). FIG. 5c shows the cover member body and cover member insert together. Here, cover member body 1100 has grooves 1150 into which opposing tongue portions 1250 of cover member insert 1200 is slidingly received.

Figure 5C:
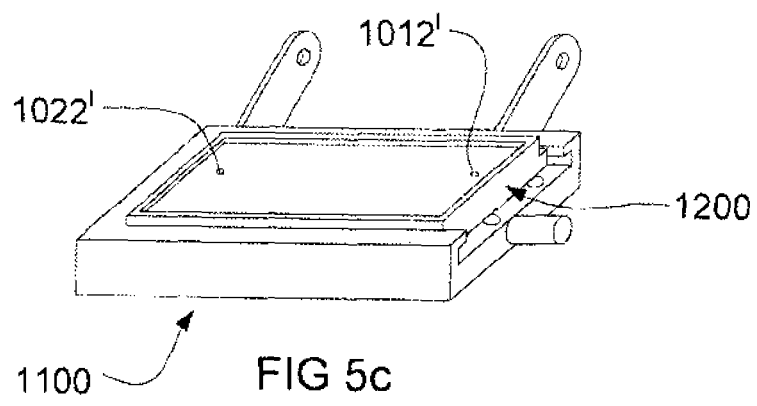

Inlet 1012 in cover member body 1100 is arranged to couple with inlet extension 1012' in the cover member insert. Similarly, outlet 1022 in the cover member body is configured to couple with the outlet extension 1022' in FIG. 5b. Coupling of the inlet/inlet extension and outlet/outlet extension in this way facilitates dispensing of a reagent in to the chamber formed by the cover member insert 1200 having a void 1124 which, when juxtaposed with a slide 200 (FIGS. 6a to 6c) forms a reagent chamber. While the arrangement shown in FIGS. 5a to 5c provide a coupling between the cover member body and cover member insert which permits sliding engagement, it is to be understood that other arrangements are also contemplated such as e.g. magnetic and suction couplings between the elements comprising a cover member.

FIGS. 6a to 6c show a treatment module 5000 according to an embodiment of the invention. The treatment module 500 includes a support surface 5100 on which a slide 200 is supported. Optionally, a thermal exchanger in the form of a heating/cooling pad 5300 (as described above) is provided between the support surface 5100 and the slide 200 to alter the temperature of reagents within the chamber during a treatment protocol. Slide 200 sits beneath the second surface 1120 of the cover member/cover member insert. FIGS. 6a to 6c also show an actuating arm 5110 for positioning the cover member 1000 in juxtaposition with the slide 200. A clamp member 3200 is provided to retain the cover member 1000 and slide 200 in juxtaposition for the duration of a treatment protocol. The clamp member 3200 may be, for example, a torsional spring that exerts a force on the cover member 1000.

Although the illustrated embodiment show the actuating arm 5110 positioned on the longer side of the cover member 1000, it is to be understood that the actuating arm may also be located at an end of the cover member. Thus the arm 5110 may be operable to open and close the cover member 1000 longitudinally.

In addition to performing advanced staining protocols, a cover member 1000 incorporating a removable/replaceable cover member insert 1200 may be useful in applications involving Polymerized Chain Reaction (PCR) protocols. In these, protocols, carryover of debris from one protocol to another can lead to contamination and failure of test samples. Accordingly, it is necessary to thoroughly clean or otherwise preclude carryover from one test to the next. Thus, incorporating a removable and ideally, disposable cover member insert 1200 into the cover member 1000 may eliminate or at least reduce the risk of debris carry over or cross-contamination and so may be desirable for applications such as PCR.

Figure 7B:
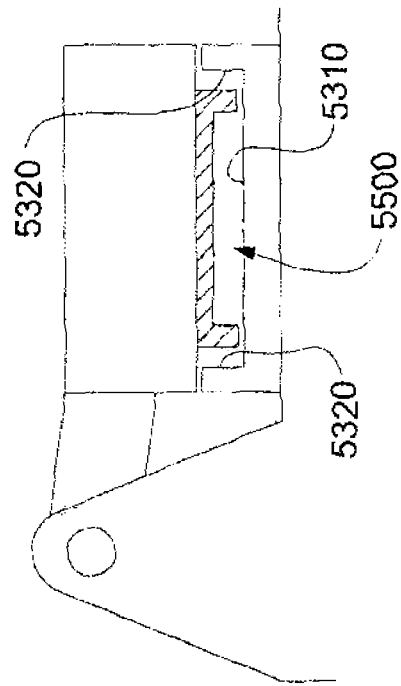
FIGS. 7a and 7b are schematic sectional views of a treatment module according to another embodiment of the invention, with a removable cover member insert and wash bay.
Figure 7A:
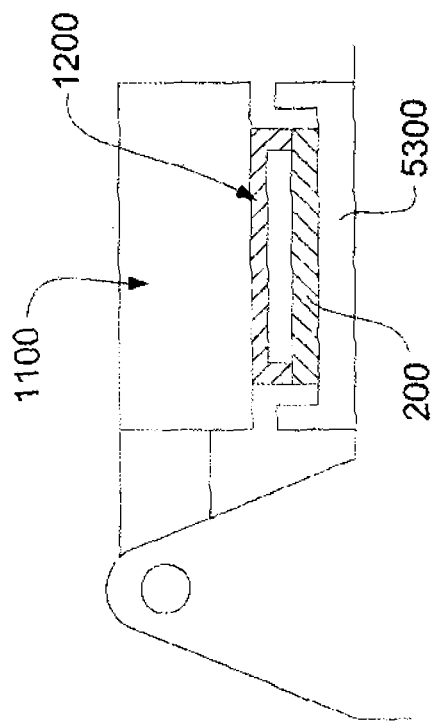

FIGS. 7a and 7b are schematic illustrations of another embodiment of the cover member also showing the actuating arm 5110. Cover member body 1100 is shown with a cover member insert 1200. FIG. 7a shows treatment module 5000 with a slide 200 retained on a heater pad 5300 on the support surface 5100. In FIG. 7b, slide 200 has been removed and surface 5310 and walls 5320 of heater pad 5300 form a wash bay 5500. Thus, once the slide 200 has been removed at the conclusion of a treatment protocol, the second surface of the cover member (or cover member insert) can be immersed within wash bay 5500 for cleaning. The cleaning reagent may be dispensed via the cover member inlet 1012/1012' and withdrawn through the outlet 1022/1022'. Alternatively, cleaning reagent may be dispensed directly into the wash bay 5500 and drained through a waste in the wash bay which is plumbed to a waste receptacle on board the instrument or via a secondary inlet port (not shown). In such arrangement, the cover member insert may be semi-disposable e.g., it may be configured for replacement every 5, 10, 15, 20 or more protocols.

In a preferred embodiment, a treatment module 5000 further includes retention means (see e.g. FIG. 12) configured to retain the slide 200 on the support surface 5100 during removal of the cover member 1000 at the conclusion of a protocol. The substrate retention means may be particularly important for overcoming the forces of sticktion that may develop between the slide surface and the cover member/cover member insert due to reagent remaining within the chamber.

Advantageously, the cover member of FIGS. 1 to 7 requires only 2 movements while the slide is in the instrument. One movement applies the cover member to the slide and the other movement is to remove the cover member from the slide to provide access so that the treated slide may be removed and/or a new slide inserted. Minimising the number of movements required of robotics within an automated instrument reduces the turnaround time required to complete a protocol for a particular sample as well as reducing instrument complexity. Additionally, in an embodiment utilising positive pressure to force reagent into the chamber, fluid dispenses are faster since the wait time for the chamber to fill under capillary action may be reduced or eliminated. Vacuum assisted filing also increases throughput for sample processing.

Figure 8:
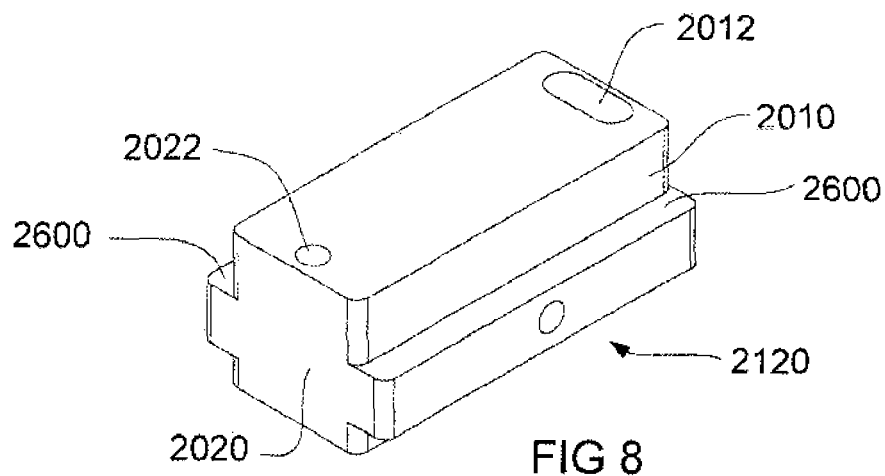
FIG. 8 is an isometric view of a cover member according to another aspect of the present invention.

FIGS. 8 to 15 illustrate a cover member according to another aspect of the invention. FIG. 8 shows a cover member 2000 which, like cover member 1000, has first end 2010, second end 2020, first surface 2110 and second surface 2120. An inlet 2012 is provided toward the first end and an outlet 2022 is provided toward the second end. Inlet 2012 is in the form of a through bore (not shown), as is outlet 2022. FIGS. 9*a* and 9*b* provide end sectional and side views respectively, of cover member 2000. The inlet profile may vary, e.g. as illustrated in FIGS. 4*a* to 4*e* such that multiple dispenses may be received by the well. Dispensing nozzles need not contact the inlet.

Figure 9A:
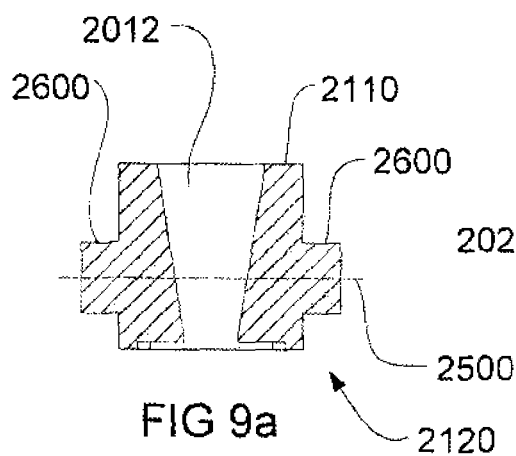
FIGS. 9a to 9c are end sectional, side and bottom views of the cover member of FIG. 8.
Figure 9B:
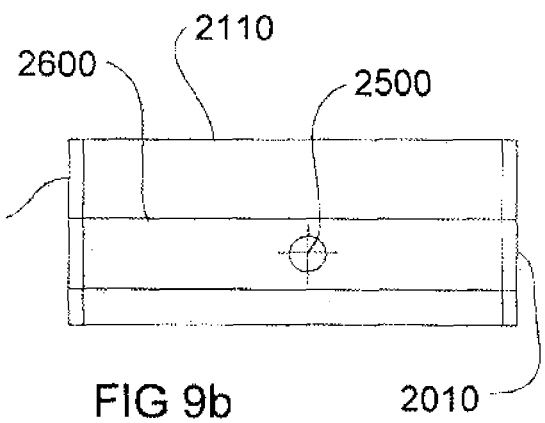
Figure 9C:
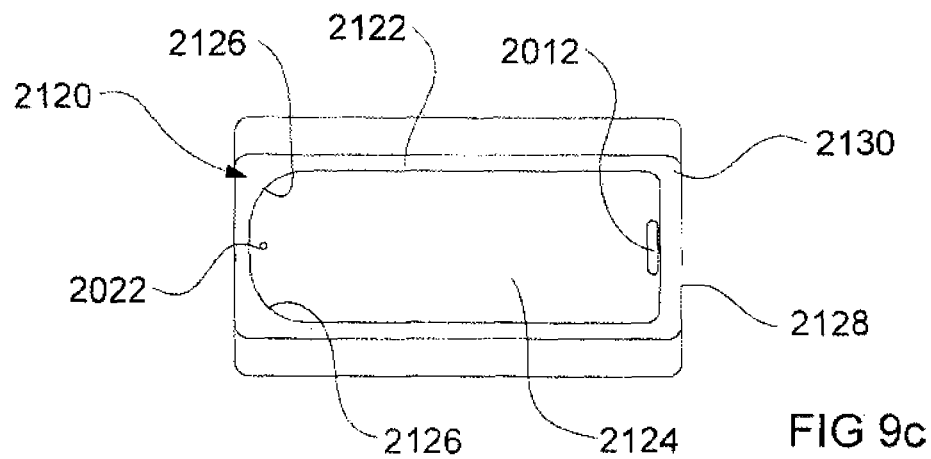

A pivot axis 2500 extends through the cover member, perpendicular to a plane which extends orthogonally between the first and second ends. A fluid dispersing edge 2128 is provided, about which the cover member pivots. FIG. 9*c* provides a bottom view of the cover member 2000 in which the dispersing edge 2128 is visible. In use, when the cover member 2000 is in an open condition, reagent is dispensed into the inlet 2012 and drains to the interface formed by the dispersing edge 2128 and the slide 200. Ideally, the cover member second surface 2120 and slide 200 form an angle of about 10 degrees when the reagent is dispensed into the inlet although other angle openings are contemplated. Surface tension stabilises passive movement of the fluid once dispensed, while pivoting motion of the cover member 2000 about the dispersing edge 2128 facilitates movement of the reagent from the dispersing edge 2128 toward the outlet 2022. Capillary forces between the slide 200 and the cover member 2000 stabilise the fluid front as it propagates across the slide reducing bubble formation.

Like cover member 1000, cover member 2000 provides a void 2124 defined by void boundary 2122 which has contoured walls 2126 toward the second end of the cover member. The contoured walls 2126 improve filling and evacuation performance of the chamber. FIG. 9*c* shows the inlet 2012 opening into the void 2124. The large opening assists to avoid formation of bubbles which block fluid flow and can adversely affect sample staining. The area of the second surface 2120 around the void boundary 2122 forms a mating face which, when in the closed condition forms a sealing face 2130. In the closed condition, the cover member 2000 and the slide 200 are typically clamped together for a period of incubation. In this condition, reagent may also be removed by application of a vacuum at the outlet.

In prior art sample staining systems, a common problem has been collection of debris and residual reagent in the chamber boundary formed along the sealing face. Contoured boundary walls 1126 in the present invention guide reagent toward outlet 2022 reducing debris collection. It is to be understood that although outlet 2022 is shown touching the void wall 2122, such contact is not essential. Rather, the outlet opening to the void may be disposed more medially of the cover member such that its opening into the void is not aligned with the void wall.

The cover member 2000 in FIGS. 8 and 9*a*-9*c* has a shoulder 2600 which provides a surface for engaging a torsion spring of a treatment module with which the cover member may be used. The torsion spring ensures correct tilt angle of the cover member. This is further described in relation to FIG. 13.

Figure 10A:
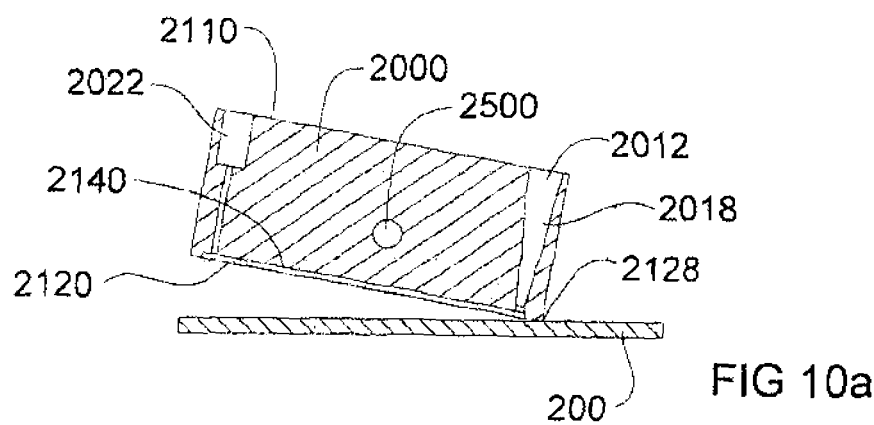
FIGS. 10a to 10d show a simplified sectional view of a cover member according to another embodiment of the invention in open, dispensing, closed and released conditions respectively, having regard to a slide.
Figure 10B:
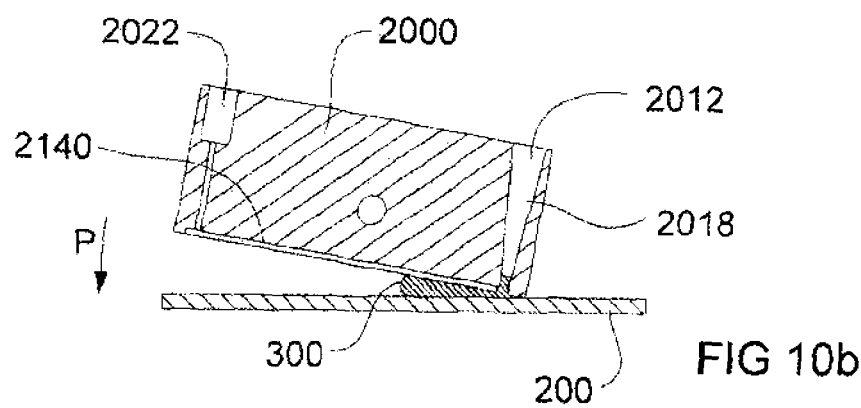
Figure 10C:
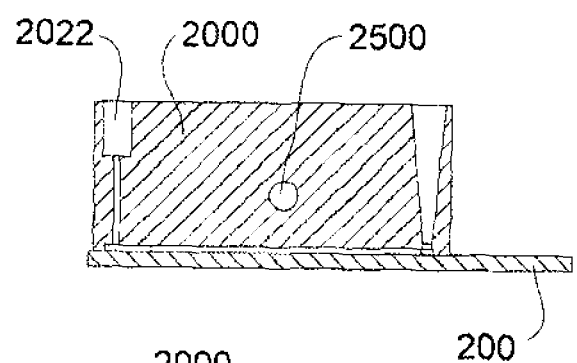

Now turning to FIGS. 10*a*-10*d*, a simplified version of cover member 2000 is shown in various dispositions relative to a slide 200. In FIG. 10*a*, the slide 200 and the cover member 2000 are positioned in an open condition in which the cover member 2000 is tilted with dispersing edge 2128 contacting slide 200. An aliquot of reagent 300 is dispensed into the inlet 2012 and the cover member 2000 is gradually pivoted toward the closed position in a direction P, causing the dispensed reagent 300 to propagate across the slide as shown in FIG. 10*b*. Preferably, the rate of pivoting the cover member 2000 is actively controlled according to the flow properties of the reagent. Actively controlling the rate of pivoting takes advantage of the capillary forces between the slide 200 and the cover member 2000. Ideally, when the cover member 2000 is in the closed position (FIG. 10*c*) the reagent has been dispensed across the entire slide surface or at least across the entire sample surface. Actively displacing the reagent using capillary action minimises the risk of formation of bubbles within the chamber.

In a preferred embodiment, the pivoting action of the cover member is controlled by a controller 7060 of an automated sample processing instrument. Typically, the controller has access to a database 7126 of pre-programmed pivoting actions which enhance or optimise reagent flow across the slide 200 for a plurality of different reagent types and/or protocols employing the various reagent types. In some such protocols, the controller 7060 may also be programmed to agitate the reagent by slight movement of the cover member 2000. Alternatively/additionally, the controller may operate a vacuum pump coupled to the cover member outlet 2020 to apply a vacuum which draws reagent across the chamber or which evacuates reagent from the chamber while the cover member is in the closed condition. The vacuum pump may also be operated in a manner which causes fluid agitation within the chamber.

Figure 10D:
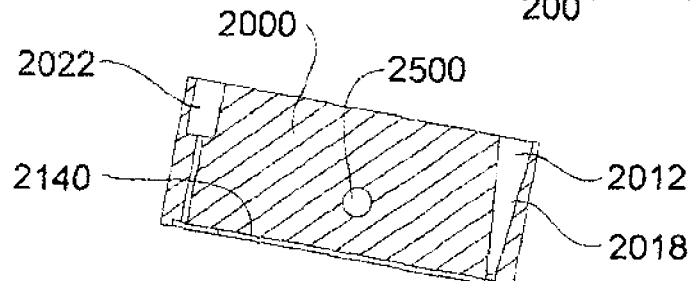
Figure 12:
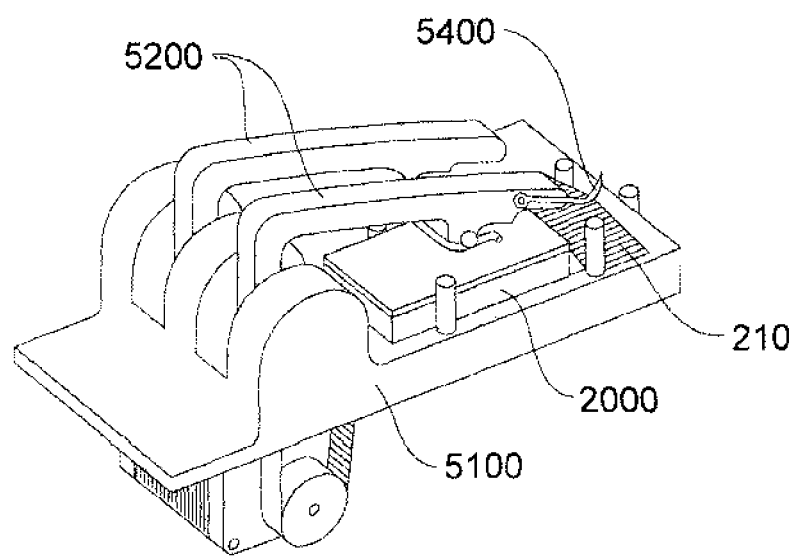
FIG. 12 is a schematic illustration of elements a treatment module for use with a cover member of the kind illustrated in FIGS. 8 to 11.

FIGS. 10*d* and 12 show the cover member in a release condition in which the cover member 2000 is separated (i.e. disassociated) from the slide 200. In this condition, a robotic arm of the instrument may load or unload a slide 200 in a treatment module 5000, or the cover member 2000 may be cleaned, removed or replaced. Cleaning the cover member in the release condition enables the entire second surface 2120 to be cleaned, including the void walls 2122 and ceiling and the cover member sealing surface 2130 that contacts the slide 200. This improves upon methods that involve cleaning the cover member while in the closed configuration e.g. by flushing, since debris from other reagents may remain along the "rails" forming the sealing interface between the slide 200 and the cover member 2000. In a preferred embodiment, cleaning of the cover member in the release condition is automated by the sample processing instrument eliminating the time consuming step of manual removal and cleaning of cover members before re-loading them into the instrument. Wash reagent may be drained from the cover member and into a waste receptacle on board the instrument, treated if hazardous, and in some embodiments may be recycled.

Figure 11:
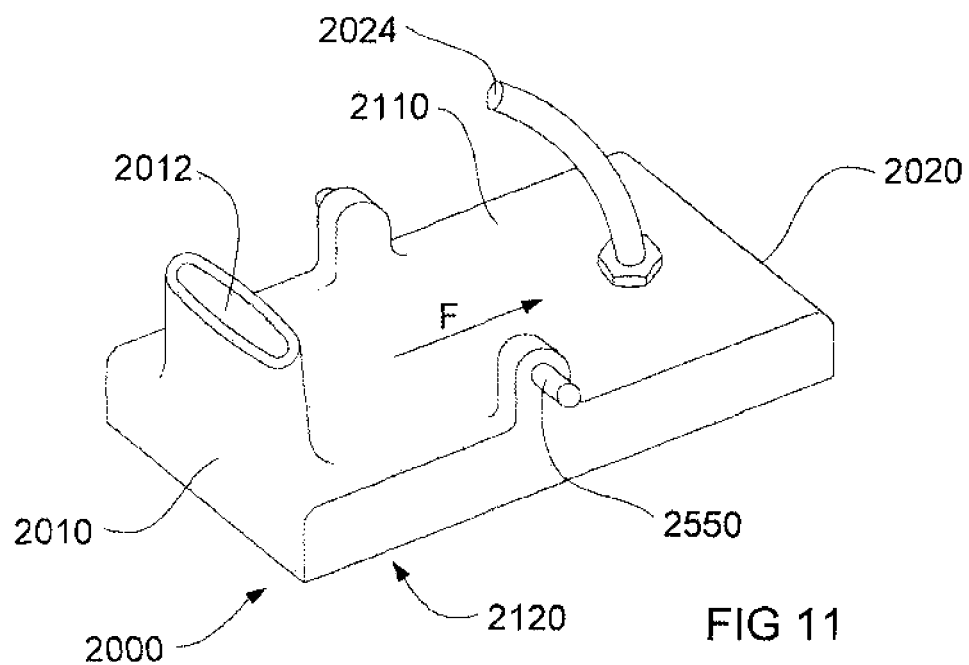
FIG. 11 is a further schematic illustration of a cover member according to an embodiment of the invention.

Now, referring to FIG. 11, a schematic illustration of a cover member 2000 is shown featuring inlet 2012, outlet 2022 with tube 2024 attached which, in a preferred embodiment, is plumbed to a waste receptacle. Reagent is dispensed, typically by a robotic arm such as a FTP or a BFR into the inlet and travels in the direction of arrow F toward the outlet. Pins 2550 disposed in first surface 2110 couple the cover member 2000 with pivot arms 5200 (see also FIGS. 13 to 15).

FIG. 12 is a schematic illustration of elements of a treatment module 5000 for treatment of a biological sample e.g. for histological staining, PCR or the like. Cover member 2000 is provided in the closed condition over a slide 200 having unique identifier region 210 bearing a barcode. Ideally, the treatment module 5000 is incorporated into an automated sample processing instrument 7000 having a reader 7068 for reading the unique identifier and associating with it a treatment protocol to be performed on the sample carried by the slide 200. Typically, the reader 7068 is in communication with a controller 7060 that has access to a database 7126 containing protocol information such as, e.g. the volume of reagent to be dispensed at various steps in the protocol, the rate at which the cover member is pivoted to maximise the capillary action drawing particular reagents across the slide, reagent incubation times and optionally incubation temperatures, agitation requirements and the like.

In a preferred embodiment, the instrument controller 7060 controls operation of pivot arms 5200 to pivot the cover member 2000 about dispersing edge 2128, gradually moving the cover member between the open (FIGS. 10a, 10b) and closed (FIG. 10c, FIG. 12) conditions. Ideally, pivot action is at a rate that optimises flow of reagent from the dispersing edge across the sample and the slide. Exploiting the capillary between the slide 200 and the void ceiling 2140 enhances this movement. Ideal pivot rate is determined, at least in part, by the viscosity of the reagent although it may also be affected by the internal finish, coating, and/or geometry of the chamber.

Figure 13:
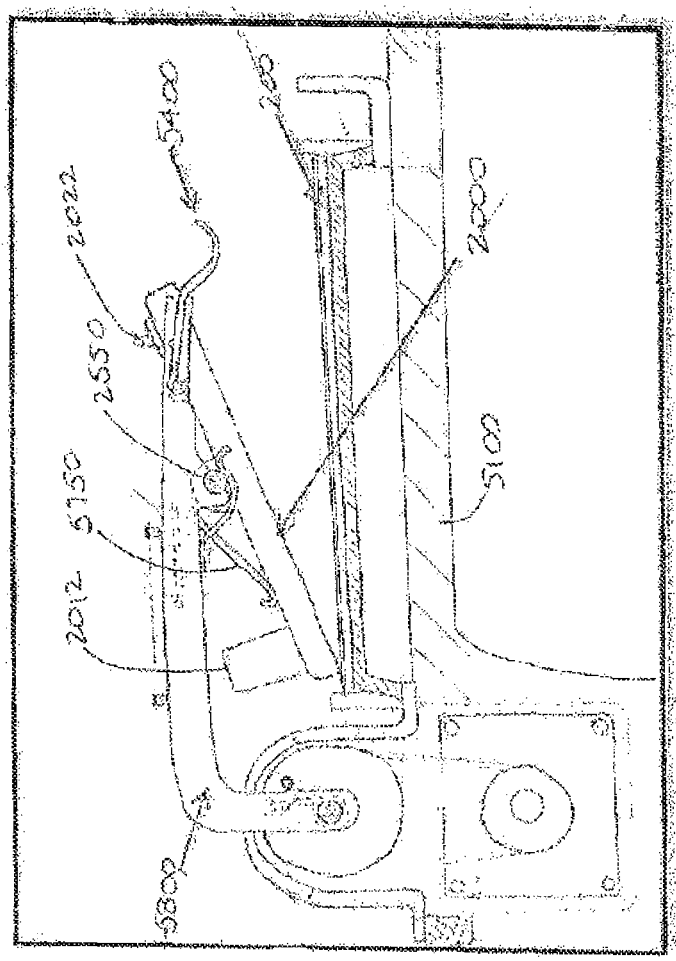
FIG. 13 is a side sectional view of a treatment module of the kind illustrated in FIG. 12.

At the conclusion of a treatment protocol, the cover member 2000 is separated from the slide and the slide is removed from the treatment module. Separation may be achieved by pivoting the cover member 2000 to the open condition and/or by displacing the cover member from the slide 200 (or vice versa) such that they are separated in the release condition (FIG. 10d, FIG. 13). In either case, reagent remaining in the chamber may give rise to sticktion forces that must be overcome in order for the slide and the cover member 2000 to be separated. Thus, in a preferred embodiment, treatment module 5000 provides slide retaining means 5400 configured to retain the slide 200 on the support surface 5100 during separation of the cover member 2000 from the slide. In the embodiment illustrated, slide retaining means 5400 is a resilient member biased toward support surface 5100 such that when cover member 2000 is in the closed condition, a portion of the slide 200 protruding from beneath the cover member is retained between the slide retaining means 5400 and the support surface 5100. However, it is to be understood that various alternatives are contemplated such e.g. retaining the slide between a prong or railing and the support surface, magnetic retaining means and the like.

FIG. 13 shows a slide view of the treatment module 5000 of FIG. 12. Cover member 2000 is coupled to pivot arms 5800 by pin 2550. Torsion spring 5750 engaging shoulders 2600 of the cover member ensure proper tilt orientation, before the cover member 2000 is moved from the release condition to the open condition, ready for receiving a reagent. Slide retaining means 5400 contacts the slide when the cover member 2000 is in the closed condition, and holds the slide 200 in place overcoming sticktion forces that may exist when the cover member and slide are separated at the conclusion of a protocol.

Figure 14:
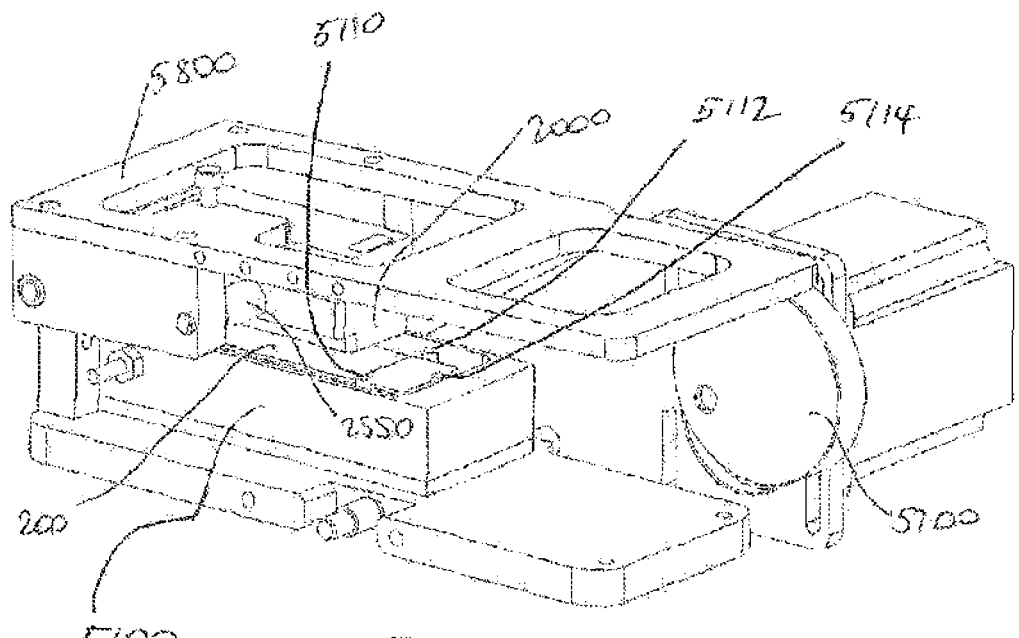
FIG. 14 is an isometric view of elements of a treatment module according to an embodiment of the invention.
Figure 15:
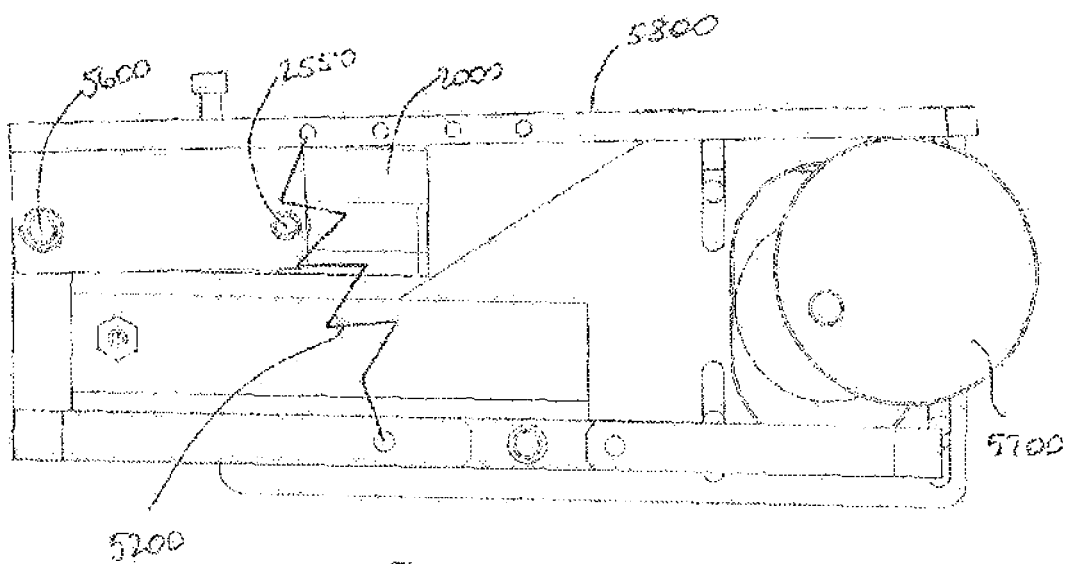
FIG. 15 is a side view of the treatment module of FIG. 14.

FIGS. 14 and 15 are schematic illustrations of elements of a treatment module according to an embodiment of the invention. A slide 200 on support surface 5100 sits beneath cover member 2000. Support surface 5100 may incorporate locating members, such as pins 5110, 5112 and 5114, that guide the substrate into position and/or act as reference points for loading substrates of different widths. Cover member 2000 is coupled to pivot arm 5800 by pin 2550. At a distal end, pivot arm 5800 contacts opening cam 5700 that pivots the arm about a second axis 5600 to displace the cover member 2000 toward or away from the slide 200 and so, is operable to move the cover member into the release condition as well as the open condition where the dispersing edge 2128 of the cover member 2000 contacts the slide. Ideally, the speed profile with which the pivot arm (or other actuating mechanism) moves is optimised such that movements while the slide 200 and cover member 2000 are disassociated are quicker than movements performed while the cover member dispersing edge is in contact with the slide and is moving from the open to the closed condition. Speed is reduced when the cover member 2000 is approaching the closed condition and when overcoming sticktion forces when opening, since it is during these movements that control is most important.

To tilt the cover member from the open condition to the closed condition, opening cam 5700 lowers pivot arm 5800 past the "open condition" point (typically forming about 10 degrees between the cover member second surface and the slide) causing cover member to rotate about pivot axis 2550. Simultaneous rotation of the pivot arm about pivot axis 5600 shifts cover member pivot axis 2550 toward the slide, such that the cover member gradually approaches the closed condition.

Advantageously, in the embodiment illustrated in FIGS. 14 and 15, only one axis of motion is required to move the cover member between the release, open and closed conditions. This has the added benefit of being able to accommodate any slide thickness. It is to be understood, however, that other arrangements which use a pivot arm to pivot the cover member between the closed and open conditions may be used. This may be in combination with e.g. a linear driver to raise and lower the pivot arm to move the cover member between the release and open conditions. Once closed, clamp means holds the cover member and the slide together, in the closed configuration, while the reagent incubates. In the embodiment illustrated, clamping means is in the form of spring 5200 although the drive mechanism employed to actuate the pivot arm could also be used to actively clamp the cover member and slide in the closed condition.

In one embodiment, a moisture barrier is provided (such as the barrier illustrated in FIG. 22), e.g. in the form of a flexible skirt or a vapour shroud to cover a sample on a substrate to mitigate the sample drying out or dehydrating when the chamber is open. Ideally, if the sample/reagent has been warmed it is cooled to ambient temperature before opening the chamber to further minimise the risk of sample dehydration. The moisture barrier may be provided as part of the cover member 2000, or as part of the treatment module 5000.

FIGS. 16 to 22 are schematic illustrations of a cover member according to yet another aspect of the present invention. The cover member includes an inlet 3012, an outlet 3022, a first end 3010 and a second end 3020. A void 3124 is bounded by void walls 3122 and an outer region of the second surface designated 3130 forms a sealing face when the cover member is brought into contact with a slide 200 (FIGS. 17 to 21). The inlet profile may vary, e.g. as illustrated in FIGS. 4a to 4e such that multiple dispenses may be received by the well. Dispensing nozzles need not contact the inlet.

Figure 17:
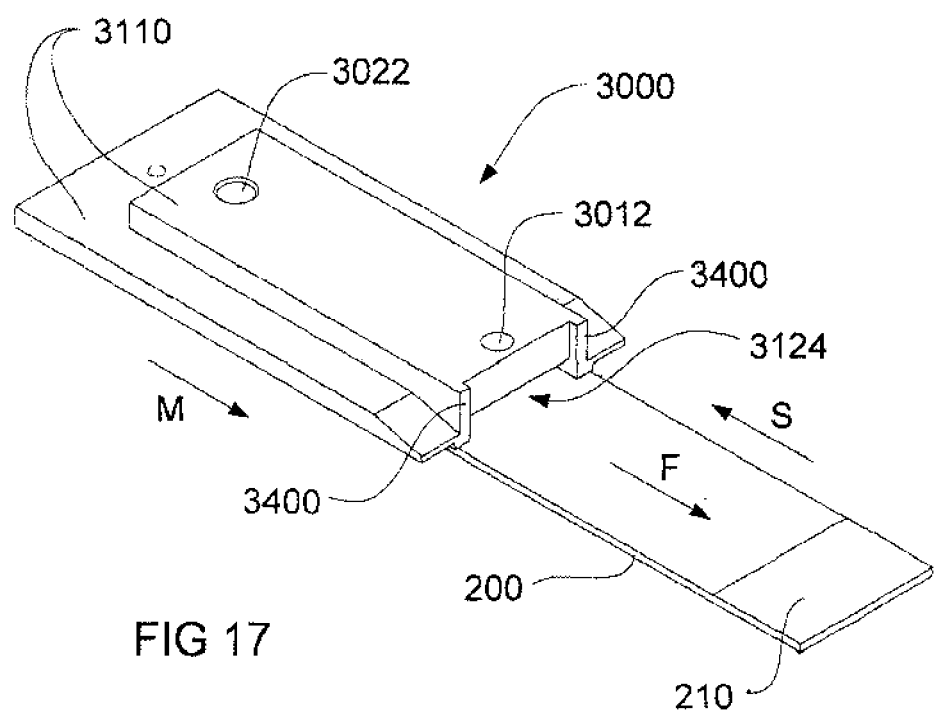
FIG. 17 is an isometric view of the cover member of FIG. 16 with a substrate in the form of a pathology slide, in an open condition.
Figure 18:
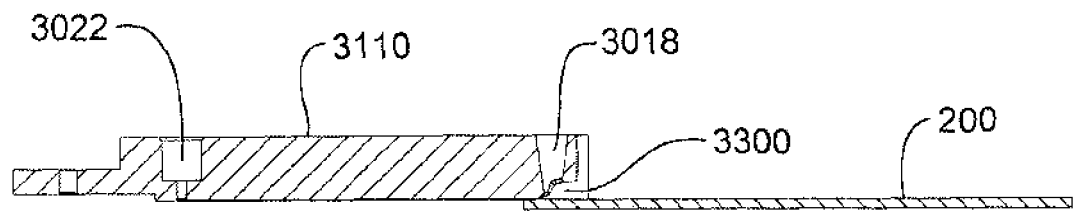
FIG. 18 is a sectional view of the cover member and substrate of FIG. 17.

The isometric view in FIG. 17 shows the first surface 3110 (i.e. top) of cover member 3000 together with a slide 200 having an identifier portion 210 for carrying a unique identifier designating the sample type or a required protocol, or a case or batch identity for the sample. As FIG. 17 shows, when cover member 3000 is placed over slide 200, void 3124 forms a chamber for receiving reagent dispensed into inlet 3012. In FIG. 17 the cover member and slide are in an open condition. FIG. 18 shows the same arrangement in longitudinal cross-section.

Preferably, the inlet is adapted to receive multiple dispenses of a reagent so as to form a reservoir 3018 as shown in FIG. 18. In another arrangement (not shown), a reagent dispense buffer capable of storing a plurality of individual reagent dispenses may be sealingly coupled with inlet 3012. The dispense buffer may comprise a barrel which is rotatable between dispense and hold positions. When rotated to a dispense position, a required volume of reagent is released into the inlet and drains into the dispersing channel where the fluid meniscus causes the reagent to wick into the space 3500 in channel 3300. Utilising a dispense buffer in this way reduces the number of individual dispenses that are required by BFR or FTP robots within an automated instrument.

Figure 16:
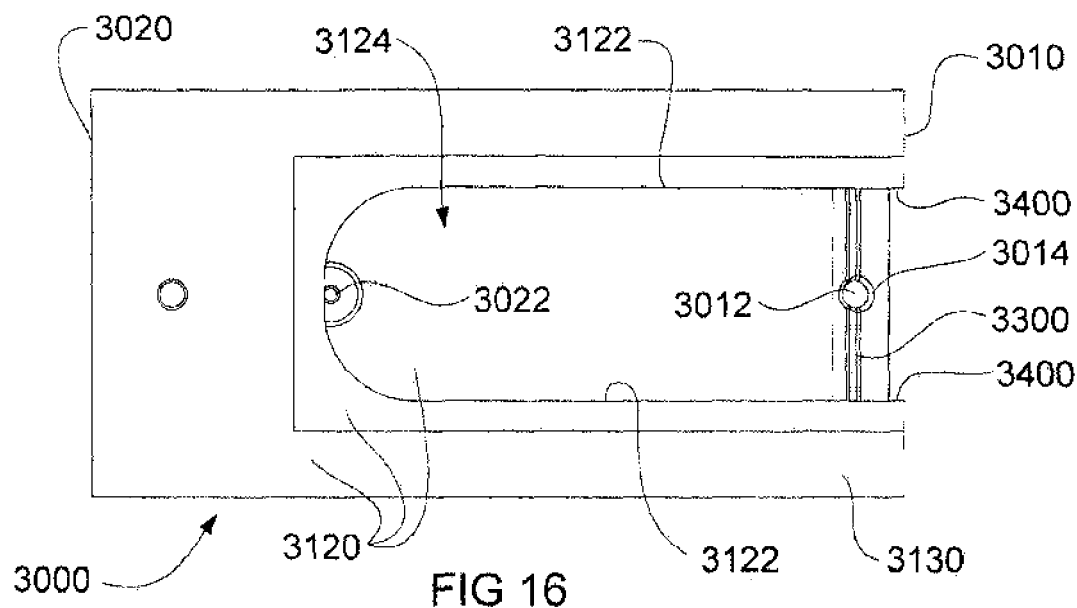
FIG. 16 is a schematic bottom view of a cover member according to another aspect of the present invention.
Figure 19:
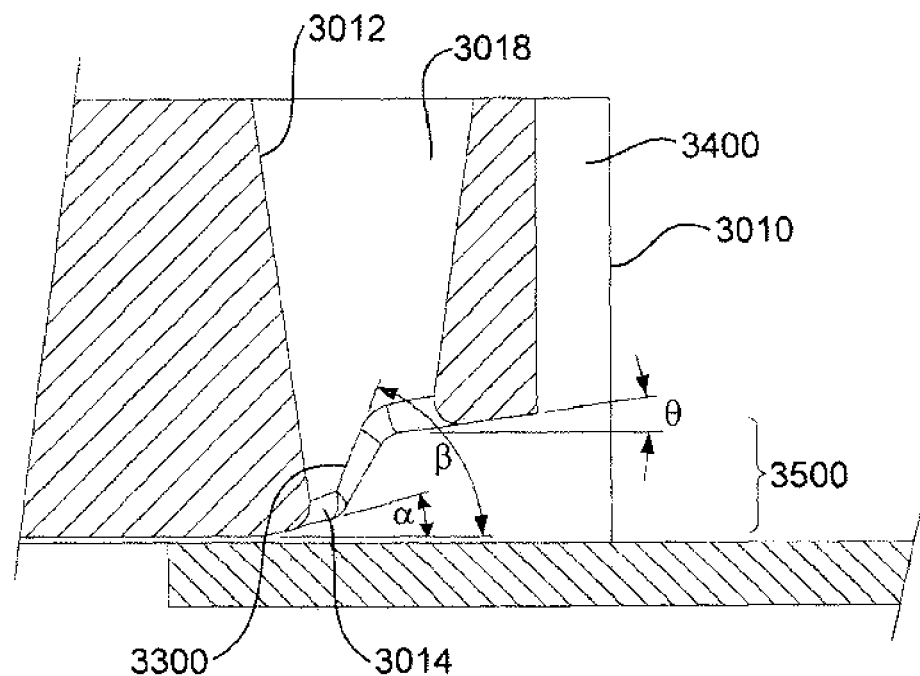
FIG. 19 is an enlarged sectional view showing the fluid dispersing feature and slide in FIGS. 16 to 18.

FIG. 19 is an enlarged sectional view showing detail of the fluid dispersing feature 3300 according to an embodiment of the invention. During use of cover member 3000, reagent is dispensed into inlet 3012 and held in reservoir 3018. Fluid in reservoir 3018 exits the inlet through inlet hole 3014 and utilising the surface tension in the fluid, fills the fluid dispersing channel 3300 which extends across the width of the slide 200 as illustrated in FIG. 16. In the embodiment illustrated in FIG. 19, the channel has a smooth stepped profile which increases in height toward the first end of the cover member. This enables the channel 3300 to retain a volume of reagent in the space 3500 which feeds a fluid front as it gradually propagates across the slide 200 during movement from the open condition to the closed condition.

In a preferred embodiment, the space 3500 has a height of approximately 2.5 mm for a chamber volume of approximately 130 µl. The stepped profile subtends angles as shown, where $\alpha$ is approximately 15 degrees, $\beta$ is approximately 60 degrees and $\theta$ is approximately 8 degrees. Additionally, contoured void boundaries 3126 (FIG. 16) preferably have a radius of approximately 9 mm. Where an outlet 3022 is provided, an outlet opening into the void having a diameter of approximately 1.3 mm has been found suitable for effective evacuation of reagent from the chamber.

A volume of reagent retained in the space 3500 is in contact with both the dispersing channel 3300 and the slide 200. The shape of the channel 3300 is contoured such that forces of surface tension within the fluid prevent it from leaking out of the channel and on to the slide. In a preferred embodiment the cover member 3000 is disposed with side walls 3400 also forming part of the fluid dispersing feature. The side walls 3400 complete the boundary of space 3500 within which the fluid wall forms.

Figure 20:
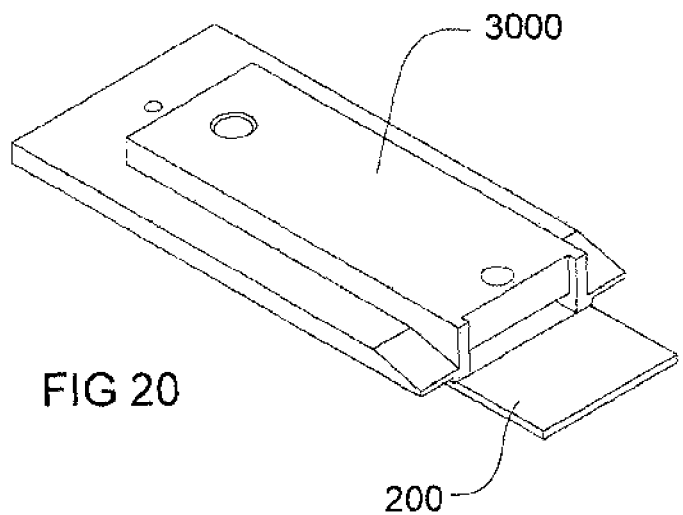
FIG. 20 is an isometric view of the cover member and substrate of FIGS. 16 to 19 in a closed condition.
Figure 21:
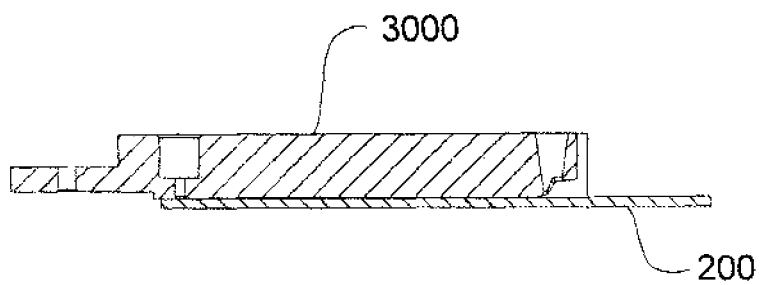
FIG. 21 is a side sectional view of the cover member and substrate of FIG. 20.

The arrangement of the channel across a width of the chamber provides a structure which facilitates dispersing of reagent across the slide 200 by slidingly moving the slide 200 and cover member 3000 into overlapping engagement. In an embodiment, this is achieved by moving the slide 200 in a direction S while the cover member 3000 is held stationary, thereby wicking fluid in the channel 3300 and space 3500 along the slide surface in the direction F. Alternatively, the cover member 3000 may be moved in a direction M while the slide 200 is held stationary. This also has the effect of drawing fluid in the dispersing channel 3300 and space 3500 along the slide surface in the direction F. Thus, in one embodiment the reagent is dispersed across the surface of slide 200 by relative movement of the slide and cover member 3000 from an open condition (FIGS. 17, 18) to a closed condition (FIGS. 20, 21). This method is hereinafter referred to as "open" dispensing.

Preferably, the rate of closing is actively controlled according to the flow properties of the reagent. Reagents having higher viscosity require a slower closing speed so that the shear forces generated during closing do not overcome the capillary/surface tension forces which hold the fluid wall within the space 3500 which feeds the fluid front as it is drawn across the slide 200. Dispensing the reagent in this way minimises the risk of formation of bubbles within the chamber 3124.

In a preferred embodiment, the sliding action of the cover member 3000 and/or slide 200 is controlled by a controller 7060 of an automated sample processing instrument 7000 of the type previously discussed. Typically, the controller has access to a database 7126 of pre-programmed sliding profiles corresponding to various reagents employed in protocols performed by the instrument. Thus, the controller 7060 is configured to control operation of an actuator which optimises reagent flow across the slide surface. An example of such a controller is shown in FIG. 25. In some protocols, the controller may also be programmed to agitate the reagent by causing small movements of the cover member or the slide while in the closed condition.

The controller 7060 is shown schematically in FIG. 25, and includes a processor 7090 in communication with a first memory device 7092 for storing computer program code and a second memory device 7094 for storing data generated by the processor 7090 when implementing the computer program code, via communications infrastructure 7096. A display interface 7098 and corresponding display 7100 enable user interaction with the controller 7060.

The controller 7060 also includes driver modules 7102 to 7112 for controlling the motors, pumps, scanners/readers, thermal exchangers and other devices 7114 to 7124 required for operation of the apparatus 7000. Treatment protocols, including staining protocols (e.g. order of reagents to be dispensed by the BFR 7014 and the FTP robot 7028 to the slides and corresponding incubation times) are stored in a protocol database 7126 accessible by the processor 7090 via the communications infrastructure 7096, enabling the processor 7090 to operate the BFR 7014 and the FTP robot 7028 to dispense re-agents to the substrates at the slide treatment stations at the required rate.

In another embodiment, fluid is dispensed while the cover member 3000 and slide 200 are in a closed condition. This is method is hereinafter referred to as "closed" dispensing and is suitable for more aqueous fluids. Closed dispensing relies on the capillary action of the fluid, and not a spreading action brought about by movement of the slide or cover member, for the reagent to disperse over the slide.

In both open and closed dispensing methods, it is necessary for the chamber formed by the cover member 3000 and the slide 200 to vent to atmosphere. In the embodiment illustrated, this vent is provided via outlet 3022 which may also be coupled via a valve or solenoid (not shown) to a vacuum source for evacuating reagent from the chamber. However, it is to be understood that an outlet 3022 in the cover member 3000 need not be provided. Instead, it is possible in the closed condition to maintain a gap between the slide 200 and the cover member second end 3020 such that the chamber is not completely closed. Omitting the outlet 3022 in this way and instead providing a gap between the slide and cover member such that the chamber directly vents to atmosphere simplifies cover member design and manufacture, but at the expense of a vacuum coupling site.

A reagent dispense step in a sample treatment protocol may be followed by dispensing of a second reagent. This may be preceded by evacuation of the chamber by connecting a vacuum at the outlet 3022. Evacuation is enhanced by contoured void boundaries 3126 (FIG. 16), which encourage evacuation of reagent from the edge of sealing face 3122.

Figure 22:
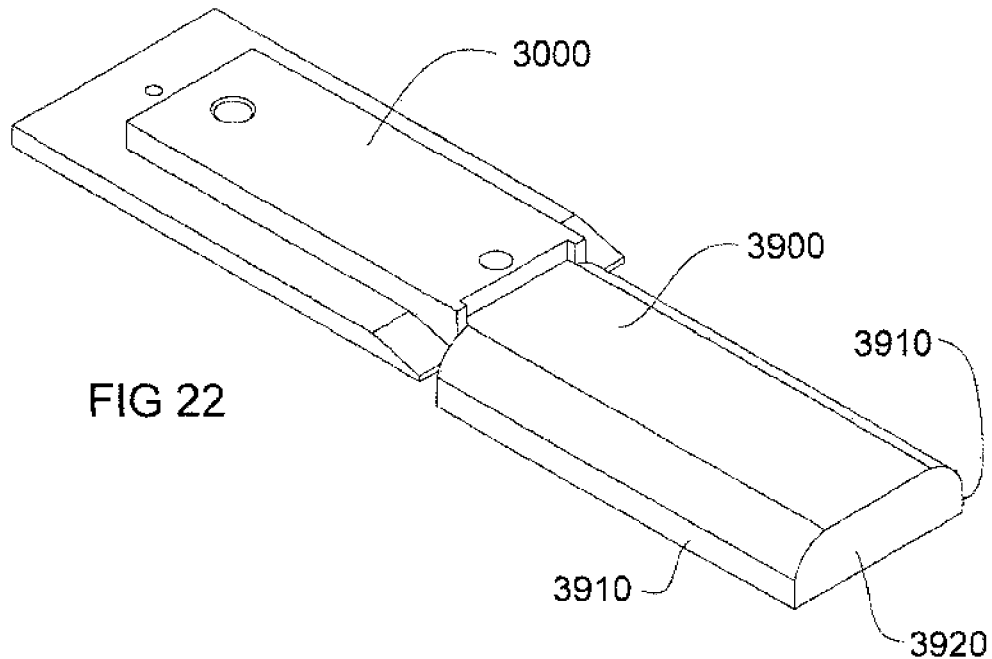
FIG. 22 is an isometric view of the cover member and substrate of FIG. 17 with a moisture barrier in the form of a physical shroud.

In a preferred embodiment, the cover member 3000 is provided with a moisture barrier 3900 to control or limit evaporation of moisture from the sample once the reagent has been dispensed over slide 200 and the cover member has been moved to the open condition. An example of a moisture barrier in the form of a physical shroud 3900 is illustrated in FIG. 22. Provision of a shroud in this way limits the amount of moisture that can dissipate from the tissue sample once the chamber has been opened. In the embodiment shown in FIG. 22, the moisture barrier 3900 is adapted to cover the entire length of the slide. However, this may not be necessary. A moisture barrier which extends only part way over a slide 200 may be sufficient to limit evaporation to an extent which preserves the integrity of the sample between reagent application and/or before it is cover-slipped and despatched for further processing.

It is desirable that the moisture barrier 3900 does not interfere with a sample on the slide. Accordingly, the moisture barrier 3900 in FIG. 22 comprises a substantially rigid canopy having wall sections 3910 supporting the canopy top. Front section 3920 may be open or closed. It is to be understood however that the moisture barrier 3900 need not be a rigid or semi-rigid structure. Rather, it may be a flexible skirt or apron which extends over the slide when in the open configuration. Further, it is to be understood that the moisture barrier may, in certain embodiments, form part of or be attached to a treatment module with which cover members are used, rather than the cover member per se. Where the moisture barrier is flexible, it is desirable for it to be supported so as to maintain a gap between the moisture barrier and the sample on the slide so as to not contaminate or disrupt the sample. In other embodiments still, the moisture barrier may be a vapour shroud comprised of a gas or aerosolised water or other suitable fluid to maintain moisture within the sample, once it has been exited from the chamber.

Figure 23:
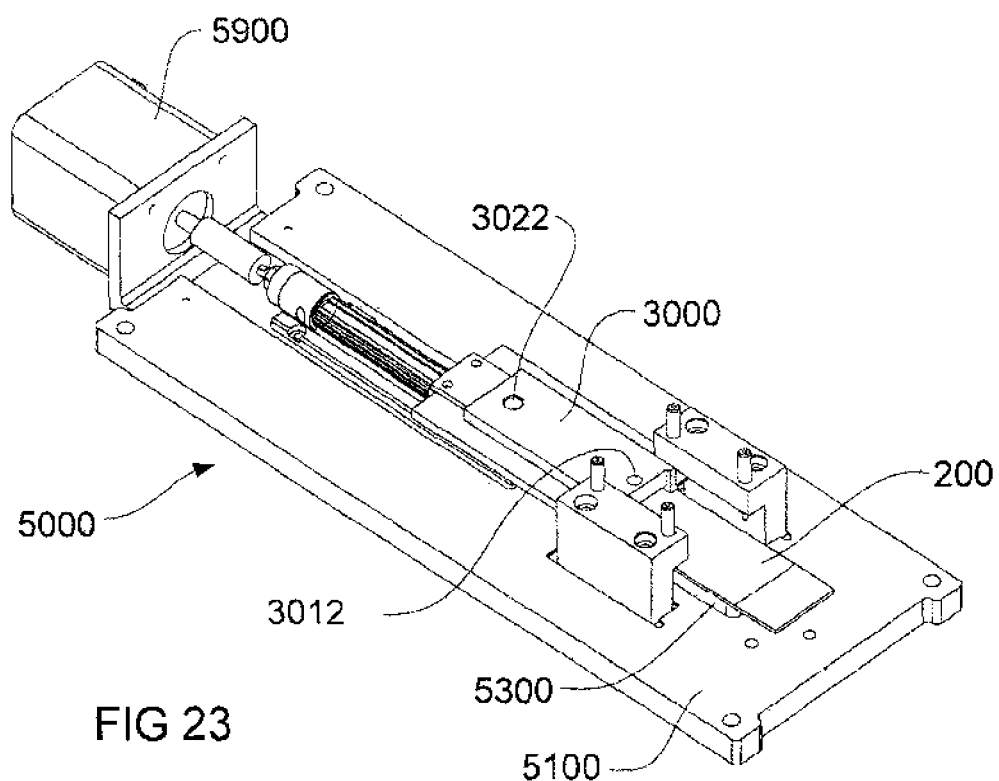
FIG. 23 is an isometric view of components of a treatment module for use with the cover member of FIGS. 16 to 22.

FIG. 23 illustrates an example of a treatment module 5000 adapted for use with the cover member 3000 in which a linear actuator 5900 slides the cover member from an open condition, over slide 200 and into a closed condition to disperse reagent dispensed into inlet 3012 over the sample carried by the slide.

In various aspects, the cover member of the present invention may be adapted to permit agitation of fluid within the chamber. Agitation may be desirable to encourage movement of fluid molecules in the chamber so that there is effective exchange between the surface of the slide (supporting the sample to be processed) and the fluid molecules. Thus, agitation of the fluid may lead to more effective processing yet with smaller reagent volumes within the chamber. Agitation may also increase the rate of reaction for a particular step in a treatment protocol, thereby reducing turnaround time between steps. Additionally, agitation of fluid within the chamber may reduce the impact of bubbles by moving the bubbles about within the chamber to ensure that every surface of the sample is exposed to the reagent fluid during the incubation period. Agitation may be achieved using various means including positive and/or negative pressure applied to an inlet and/or outlet port, introduction and/or withdrawal of fluid from an inlet and/or outlet port or other such means that facilitate the flow of fluid via the inlet and/or outlet ports to generate a turbulence sufficient to promote agitation of the fluid.

Furthermore, fluid agitation may reduce staining artefacts resulting from the presence of bubbles, enhance uniformity of reagent throughout chamber, minimize "dead zones", facilitate in situ cleaning and/or washing of a surface of the cover member. Movement of fluid within the chamber may be enhanced by contoured geometry of the chamber walls (e.g. as described with reference to FIG. 1). The contours may be provided toward an inlet end of the cover member to enhance fluid flow and, when provided toward the outlet end may provide improved evacuation of fluid from the chamber, such that minimal debris remains. Alternatively/additionally, one or both ends of the chamber may be defined by the void walls forming a taper or curved end wall. Additionally, it may be desirable to provide a finish on the void ceiling which enhances reagent propagation within the chamber. The finish may comprise of a texture such as e.g. corrugation, etching, dimpling or arrow contours in the second surface forming the void ceiling. Sloping the void ceiling or bowing it or providing ripples within the ceiling may also enhance fluid flow. Alternatively/additionally, the void ceiling and/or walls may be coated or treated with a material finish that enhances fluid flow.

Various features of the present invention give rise to cover members which minimise the amount of reagent required for performing steps of treatment protocols of the kind employed by instrument 7000. Ideally, various aspects of the present invention facilitate an effective reaction chamber formed by the cover member which has a volume as small as 120 to 135 µl. Although, closed volumes as small as 30 µl are also contemplated. In some reactions, it may be necessary to provide a larger reaction chamber having closed volumes of e.g. up to 200 µl.

In one or more embodiments, liquid level sensing for reagents dispensed into the inlet may be desirable. Liquid level sensing may be performed using probe touch technology and/or by monitoring changes in capacitance or pressure at a dispensing probe tip. Alternatively, optical liquid level sensing systems and ultrasonic systems may be employed. Measurements of reagent volumes taken at the inlet, in the chamber and/or through the outlet, can be compared by a controller 7060 on board an automated instrument 7000 to cross check against the volume of dispenses calculated according to the number of protocols performed. This cross check can then be used for inventory control of reagents stored on board the automated instrument.

Although the various cover member embodiments illustrated herein demonstrate only one outlet, it is to be understood that a plurality of outlets could be provided. However, where a vacuum is applied to enhance fluid movement (including agitation) within the chamber and/or evacuate reagent from the chamber, separate vacuum sources are required for each of the outlets. Thus, in designing a cover member according to the present invention, the skilled addressee will balance complexity and price with performance. Although each of the one or more outlets may be coupled to a vacuum source, embodiments utilising forced pressure dispensing (FIGS. 1 to 3) and capillary dispensing, require that the chamber be vented to atmosphere. Accordingly, the outlet may be interchangeably coupled with a vacuum source and a vent to atmosphere.

Use of a vacuum during filling of the chamber may reduce the likelihood of bubbles forming within the chamber. Moreover, use of a vacuum to evacuate fluid from the chamber reduces the likelihood of debris remaining within the chamber between reagent dispenses. Another advantage of using a vacuum to evacuate reagent from the chamber is that less reagent may be used, since evacuating the chamber before application of the second reagent minimises the risk of mixing.

Ideally, the automated instrument controller 7060 accesses a database 7128 of protocol information which is used to control the one or more vacuum sources to apply the correct magnitude and duration of vacuum, depending on the reagent used (e.g. viscous or aqueous) and/or the sample type or section thickness (e.g. skin sample or cytology sample may range in thickness from 1 µm to 15 µm, and preferably 3 µm to 5 µm).

It is to be noted the inlet may be formed in the cover member body in any orientation, and may exit the cover member on any surface, although in the embodiments illustrated the inlet opening is provided on the first (i.e. top) surface of the cover member. Additionally, it is to be noted that although each embodiment is illustrated with one inlet, provision of multiple inlets is also contemplated. Similarly, as outlined above, multiple outlets are contemplated. It is also to be understood that those outlets may exit the cover member on any surface, although the embodiments illustrated show the outlet exiting the cover member on the first (i.e. top) surface and the front surface (FIG. 1). The location of the outlet opening may be influenced by the location of couplings and/or conduits which connect the outlet to a vacuum source and/or a valve or solenoid through which the outlet is coupled with the vacuum source and/or vented to atmosphere. Additionally, although it is not essential, locating the outlet in contact with a void boundary within the cover member may improve evacuation of reagent from the chamber.

Throughout this specification, the embodiments illustrated are described with reference to the slide being maintained in a substantially horizontal orientation. It is to be understood however, that horizontal orientation is not necessarily required and that the support surface may support the slide at an incline. Further, the invention is described in terms of propagation of fluid longitudinally, from the first end toward the second end of the cover member. It is to be understood, however, that the cover member may be configured for transverse fluid flow across the slide employing a wider fluid front although the risk of bubble formation may be higher in this configuration. It is also to be noted that the slide processing according to embodiments of the invention need not be limited to processing in a horizontal orientation.

Preferably, when the inventive cover member is used by an automated sample processing instrument, each slide being processed contains a unique identifier such as a barcode or RFID tag which identifies one or more of the sample type and a protocol to be performed on the sample. That information is detected by a reader device in the instrument and used to schedule dispense actions of BFR and FTP robots within the instrument, according to the required protocol.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

The claims defining the invention are as follows:

1. A treatment module for a biological sample, the module comprising:
 a cover member having;
  i. opposing ends comprising a first end and a second end;
  ii. opposing surfaces comprising a first surface and a second surface;
  iii. a void in the second surface which, when juxtaposed with a substrate, forms a chamber; and
  iv. a fluid inlet toward the first end and in fluid communication with the void;
 a support surface configured to support the substrate and a biological sample thereon; and
 a pivot arm configured to pivot the cover member about a dispersing edge causing fluid to move from the inlet along the substrate from the dispersing edge toward a fluid outlet, the pivot arm being operable to pivot the cover member to an open condition and to a closed condition, wherein
 the pivot arm is operable to pivot the cover member and lift the cover member away from the support surface such that, of the first and second opposing ends, only one of the first and second opposing ends is lifted away from the support surface.

2. The treatment module according to claim 1, comprising a robot configured to position one or both of the substrate and the cover member in the treatment module and optionally, wherein the robot is configured to dispense reagent into an inlet of the cover member during a treatment protocol.

3. The treatment module according to claim 1, comprising a coupling operable to interchangeably connect one or more outlets, including the fluid outlet, of the cover member with one or more of a vent to atmosphere and a respective one or more negative pressure sources.

4. The treatment module according to claim 1, further comprising a substrate retention member configured to retain the substrate on the support surface during opening of the chamber or separation of the cover member and the substrate.

5. The treatment module according to claim 1, wherein the treatment module is configured for use with an automated sample processing instrument comprising a plurality of treatment modules operable independently under control of a controller of the instrument; and wherein operation of one or more of a clamp, a thermal exchanger, a robot, a negative pressure source and fluid dispenser is under the control of the instrument controller.

6. The treatment module according to claim 1, further including a wash bay for exposing a surface of the cover member to a wash reagent, wherein optionally, the support surface is shaped to receive a substrate having a sample thereon and, in the absence of a substrate, to form the wash bay.

7. A method for incubating a biological sample with one or more reagents using a cover member according to claim 1, including the steps of:
   a. providing the sample on a substrate;
   b. positioning the substrate and the cover member to form the chamber;
   c. positioning a dispensing probe tip in mating contact with a fluid inlet of the cover member; and
   d. driving a first volume of a first reagent into the inlet with force sufficient for the first reagent to substantially cover the sample on the substrate; and optionally agitating reagent within the chamber;
   e. agitating reagent within the chamber.

8. A method according to claim 7, including one or more further steps comprising:
   a. applying a negative pressure at a fluid outlet of the cover member to draw reagent within the chamber toward the outlet; and
   b. removing the substrate from a support surface and immersing a second surface of the cover member in a wash reagent.

9. A method for incubating a biological sample with one or more reagents using a treatment module according to claim 1, including the steps of:
   a. providing the sample on a substrate;
   b. positioning the substrate and a cover member to form a chamber;
   c. positioning a dispensing probe tip in mating contact with a fluid inlet of the cover member; and
   d. driving a first volume of a first reagent into the inlet with force sufficient for the first reagent to substantially cover the sample on the substrate; and optionally
   e. agitating reagent within the chamber.

10. A method according to claim 7, including one or more further steps comprising:
    a. applying a negative pressure at an outlet of the cover member to draw reagent within the chamber toward the outlet and
    b. removing the slide from a support surface of the treatment module and immersing a second surface of the cover member in a wash reagent.

11. The treatment module according to claim 1 wherein the cover member is removable from the treatment module.

12. The treatment module according to claim 1 wherein the cover member void is bounded by void walls having one or more contoured regions for enhancing fluid movement within the chamber.

13. The treatment module according to claim 1, wherein the cover member includes:
    the fluid outlet toward the second end and in fluid communication with the void; and
    a guide at the inlet, configured to direct fluid into the inlet.

14. The treatment module according to claim 1, wherein the cover member includes:
    the fluid outlet, the fluid outlet being disposed toward the second end and in fluid communication with the void; and
    the dispersing edge, the dispersing edge being disposed in fluid communication with the fluid inlet;
    wherein the cover member is adapted to pivot about the dispersing edge causing movement of the fluid in the fluid inlet from the dispersing edge toward the fluid outlet.

15. The treatment module according to claim 1, wherein the cover member includes a fluid dispersing feature from which fluid is dispensed, wherein the fluid dispersing feature is configured to dispense fluid from the inlet onto at least a width of the substrate.

16. The treatment module according to claim 1, wherein the cover member further comprises the fluid outlet toward the second end and in fluid communication with the void and through which fluid may be withdrawn.

17. The treatment module according to claim 1, wherein the cover member void is bounded by void walls having one or more contoured regions and the one or more contoured regions comprise rounded corners connecting side walls of the void with an end wall of the cover member to encourage fluid flow within the chamber.

18. The treatment module according to claim 1, wherein the cover member void is bounded by void walls having one or more contoured regions and wherein the one or more contoured regions comprise a rounded taper connecting side walls of the void with an end wall of the cover member to encourage fluid flow within the chamber.

19. The treatment module according to claim 1, wherein the cover member void is bounded by void walls having one or more contoured regions and wherein the one or more contoured regions comprise rounded cornices connecting the walls of the void with a void ceiling in the second surface of the cover member.

20. The treatment module according to claim 1, wherein a void ceiling in the second surface of the cover member has a finish configured to enhance reagent propagation from the fluid inlet to the fluid outlet, and optionally, wherein the finish is at least one of etched, corrugated, dimpled, sloped, bowed, and rippled.

21. The treatment module according to claim 1, wherein the cover member is disposable.

22. The treatment module according to claim 1, wherein the cover member is formed from at least two parts including a cover member body and a cover member insert, wherein the cover member insert is configured to form the chamber with the substrate; and optionally, wherein the cover member insert is disposable.

23. The treatment module according to claim 1, including a guide configured to form a snug fit with a dispensing probe tip.

24. The treatment module according to claim 23, wherein the guide has compliance sufficient to receive and form a seal with a dispensing probe tip.

25. A treatment module for a biological sample, the module comprising:
    a cover member having;
      i. opposing ends comprising a first end and a second end;
      ii. opposing surfaces comprising a first surface and a second surface;
      iii. a void in the second surface which, when juxtaposed with a substrate, forms a chamber; and
      iv. a fluid inlet toward the first end and in fluid communication with the void;
    a support surface for a substrate having a biological sample thereon;
    an actuating arm attached to the cover member and located at the first end or the second end thereof to position the cover member in an open condition and in a closed condition, the closed condition being a position in which the cover member and the substrate are juxtaposed to form the chamber, the actuating arm being connected to a clamp that resiliently biases the cover member in juxtaposition with the substrate for an incubation period; and a torsional spring attached to the cover member from the actuating arm and configured to exert a force on the cover member towards the substrate, and wherein the fluid inlet extends through the cover member.

26. The treatment module according to claim 1, wherein the pivot arm comprises pins extending from the pivot arm and coupling the cover member to the pivot arm.

27. The treatment module according to claim 1, wherein the pivot arm is configured such that pivoting the cover member from the closed condition to the open condition lifts the first opposing end of the cover member from the substrate without lifting the second opposing end of the cover member from the substrate, wherein the first end of the cover member comprises the fluid outlet, and wherein the second end of the cover member comprises the fluid inlet and the dispersing edge.

28. The treatment module according to claim 1, wherein the cover member comprises the dispersing edge at the fluid inlet, and wherein the fluid inlet comprises a step which increases in height, along a longitudinal axis of the fluid inlet through the cover member, and narrows the fluid inlet towards the dispersing edge of the fluid inlet.

29. The treatment module according to claim 28, further comprising the substrate, and wherein, in the closed condition in which the cover member is sealed to the substrate, a lower portion of the step at the dispersing edge forms a 15° angle with respect to the substrate and an upper portion of the step away from the dispersing edge form a 8° angle with respect to the substrate, and wherein the step comprises a 60° angle from the lower portion to the upper portion with respect to the substrate.

30. The treatment module according to claim 1, further comprising:

a controller configured to implement controlling the pivot arm:

to pivot the cover member about the dispersing edge, to pivot the cover member to the open condition and to the closed condition, and to pivot the cover member from the closed condition to the open condition by lifting at least part of the cover member from the substrate.

31. The treatment module according to claim 25, wherein the fluid inlet extends through the cover member from the first surface to the second surface.

32. The treatment module according to claim 1, wherein the pivot arm is further operable to lift the cover member from the substrate while maintaining contact between the dispersing edge and the substrate by pivoting the cover member along a longitudinal axis of the cover member with respect to a longitudinal axis of the substrate.

33. The treatment module according to claim 32, wherein the dispersing edge of the cover member is at a longitudinal end side of the cover member.

34. The treatment module according to claim 28, wherein the longitudinal axis of the fluid inlet is perpendicular to the longitudinal axis of the cover member, and wherein the fluid inlet gradually narrows from a part of the step, furthest from the substrate, up to the dispersing edge.

35. The treatment module according to claim 31, wherein the torsional spring extends from the cover member to at least one of the pins.

* * * * *